US009677129B2

(12) United States Patent
Economides et al.

(10) Patent No.: US 9,677,129 B2
(45) Date of Patent: Jun. 13, 2017

(54) METHOD FOR DETECTING THE REPLACEMENT OF AN ENDOGENOUS ALLELE WITH A MODIFIED ALLELE BY HOMOLOGOUS RECOMBINATION IN A MOUSE ES CELL

(71) Applicants: Aris N. Economides, Tarrytown, NY (US); Andrew J. Murphy, Croton-On-Hudson, NY (US); David M. Valenzuela, Yorktown Heights, NY (US); David Frendewey, New York, NY (US); George D. Yancopoulos, Yorktown Heights, NY (US)

(72) Inventors: Aris N. Economides, Tarrytown, NY (US); Andrew J. Murphy, Croton-On-Hudson, NY (US); David M. Valenzuela, Yorktown Heights, NY (US); David Frendewey, New York, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 293 days.

(21) Appl. No.: 14/193,393

(22) Filed: Feb. 28, 2014

(65) Prior Publication Data
US 2014/0178879 A1 Jun. 26, 2014

Related U.S. Application Data

(63) Continuation of application No. 11/809,473, filed on Jun. 1, 2007, now Pat. No. 8,759,105, which is a
(Continued)

(51) Int. Cl.
*C12Q 1/68* (2006.01)
*A01K 67/027* (2006.01)
(Continued)

(52) U.S. Cl.
CPC ........ *C12Q 1/6827* (2013.01); *A01K 67/0275* (2013.01); *C12N 15/79* (2013.01);
(Continued)

(58) Field of Classification Search
CPC ........ C12N 15/90; C12N 15/79; C12N 15/00; C12N 15/09; C12N 5/10; A01K 67/027; C12Q 1/68
See application file for complete search history.

(56) References Cited

U.S. PATENT DOCUMENTS

| 5,436,149 A | 7/1995 | Barnes |
| 5,770,429 A | 6/1998 | Lonberg et al. |

(Continued)

FOREIGN PATENT DOCUMENTS

| WO | WO-90/04036 A1 | 4/1990 |
| WO | WO-91/00906 A1 | 1/1991 |

(Continued)

OTHER PUBLICATIONS

Choi and Wing. "The Construction of Bacterial Artificial Chromosome (BAC) Libraries."Plant Molecular Biology Manual H5, 1-28, 2000.*

(Continued)

*Primary Examiner* — Titilayo Moloye
(74) *Attorney, Agent, or Firm* — Brendan T. Jones; Neil Miyamoto; Foley Hoag LLP

(57) ABSTRACT

A method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. Also provided is a rapid and
(Continued)

convenient method of detecting eukaryotic cells in which the LTVEC has correctly targeted and modified the desired endogenous gene(s) or chromosomal locus (loci) as well as the use of these cells to generate organisms bearing the genetic modification.

11 Claims, 6 Drawing Sheets

Related U.S. Application Data continuation of application No. 10/415,440, filed as application No. PCT/US01/45375 on Oct. 31, 2001, now abandoned, which is a continuation-in-part of application No. 09/732,234, filed on Dec. 7, 2000, now Pat. No. 6,586,251.

(60) Provisional application No. 60/244,665, filed on Oct. 31, 2000.

(51) Int. Cl.
C12N 15/90 (2006.01)
C12N 15/79 (2006.01)

(52) U.S. Cl.
CPC ........ C12N 15/907 (2013.01); A01K 2217/05 (2013.01); A01K 2227/105 (2013.01)

(56) References Cited

U.S. PATENT DOCUMENTS

| | | | |
|---|---|---|---|
| 5,789,215 | A | 8/1998 | Berns et al. |
| 5,877,397 | A | 3/1999 | Lonberg et al. |
| 5,928,914 | A | 7/1999 | Leboulch et al. |
| 5,939,598 | A | 8/1999 | Kucherlapati et al. |
| 6,114,598 | A | 9/2000 | Kucherlapati et al. |
| 6,130,364 | A | 10/2000 | Jakobovits et al. |
| 6,586,251 | B2 | 7/2003 | Economides et al. |
| 6,596,541 | B2 | 7/2003 | Murphy et al. |
| 6,998,514 | B2 | 2/2006 | Bruggemann |
| 7,105,348 | B2 | 9/2006 | Murphy et al. |
| 7,501,552 | B2 | 3/2009 | Lonberg et al. |
| 2006/0015957 | A1 | 1/2006 | Lonberg et al. |

FOREIGN PATENT DOCUMENTS

| | | |
|---|---|---|
| WO | WO-94/02602 A1 | 2/1994 |
| WO | WO-94/04667 A1 | 3/1994 |
| WO | WO-96/30498 A1 | 10/1996 |
| WO | WO-98/24893 A2 | 6/1998 |
| WO | WO-99/45962 A1 | 9/1999 |

OTHER PUBLICATIONS

Picciotto and Wickman ."Using knockout and transgenic mice to study neurophysiology and behavior."Physiol Rev. Oct. 1998;78(4):1131-63.*
Giraldo and Montoliu "Size matters: use of YACs, BACs and PACs in transgenic animals."Transgenic Res. Apr. 2001;10(2):83-103.*
Moreadith et al. "Gene targeting in embryonic stem cells: the new physiology and metabolism."Journal of Molecular Medicine Mar. 1997, vol. 75, Issue 3, pp. 208-216.*
Kuroiwa et al. "Sequential targeting of the genes encoding immunoglobulin-mu and prion protein in cattle." Nature Genetics 36, 775-780 (2004).*
Kobayashi et al."The Minipig—A New Tool in Stem Cell Research. "Advances in Mechanisms, Methods and Models, Prof. Craig Atwood (Ed.), ISBN 978-953-51-1590-8, Published: Jul. 2, 2014.*
Pera et al. "Human embryonic stem cells."J Cell Sci. Jan. 2000;113 ( Pt 1):5-10.*

Ueda et al. "Establishment of Rat Embryonic Stem Cells and Making of Chimera Rats."PLoS One. Jul. 30, 2008;3(7):e2800.*
Abremski and Hoess, "Bacteriophage P1 Site-specific Recombination, Purification and Properties of the Cre Recombinase Protein," Journal of Biological Chemistry 259(3):1509-1514 (1984).
Andrews et al., "The FLP Recombinase of the 2μ Circle DNA of Yeast: Interaction with Its Target Sequences," Cell 40:795-803 (1985).
Angrand, P.O. et al., "Simplified Generation of Targeting Constructs Using ET Recombination," Nucleic Acids Res., 27(17): e16 (1999).
Bethke and Sauer, "Segmental Genomic Replacement by Cre-Mediated Recombination: Genotoxic Stress Activation of the p53 Promoter in Single-Copy Transformants," Nucleic Acids Res 25(14):2828-2834 (1997).
Bogen, B. et al., "A Rearranged λ2 Light Gene Chain Retards But Does Not Exclude χ and λ1 Expression." Eur. J. Immunol., 21:2391-2395 (1991).
Bouhassira, E.E. et al., "Transcriptional Behavior of LCR Enhancer Elements Integrated at the Same Chromosomal Locus by Recombinase-Mediated Cassette Exchange," Blood, 90(9):3332-3344 (1997).
Bourdeau, V. et al., "Genome-wide Identification of high-affinity Estrogen Response Elements in Human and Mouse," Mol Endocrinol. 18(6):1411-17 (2004).
Bruggemann, M. "Human Antibody Expression in Transgenic Mice," Archivum Immunologiae et Therapiae Experimentalis, 49:203-208 (2001).
Bruggemann, M. et al., "Strategies for Expressing Human Antibody Repertoires in Transgenic Mice," Review Immunology Today, 17(8):391-397 (1996).
Butler, J.E. "Immunoglobulin Diversity, B-cell and Antibody Repertoire Development in Large Farm Animals," Revue Scientifique at Technique Office International Des Epizooties, 17(1):43-70 (1998).
Cheng, S. et al., "Long PCR," Nature 369(6482):684-685 (1994).
Clark, et al., Genes of the RecE and RecF Pathways of Conjugational Recombination in Escherichia coli, National Library of Medicine, (1984), pp. 453-462.
Clark, J. et al., "A Future for Transgenic Livestock," Nature Reviews, 4:825-833 (2003).
Clark, M., "Antibody Humanization: A Case of the 'Emperor's New Clothes'?", Immunol. Today 21(8):397-402 (2000).
Cook, G.P. et al., "A Map of the Human Immunoglobulin VH Locus Completed by Analysis of the Teleomeric Region of Chromosome 14q," Nat. Genet., 7(2):162-8 (1994).
Cowan, P.J. et al., "Targeting gene expression to endothelium in transgenic animals: a comparison of the human ICAM-2, PECAM-1 and endoglin promoters," Xenotransplantation, 10(3):223-31 (2003).
Cox, "The FLP protein of the yeast 2-microns plasmid: expression of a eukaryotic genetic recombination system in Escherichia coli," Proc Natl Acad Sci USA 80(14):4223-4227 (1983).
Davies, N.P. et al., "Creation of Mice Expressing Human Activity Light Chains by Introduction of a Yeast Artificial Chromosome Containing the Core Region of the Human Immunoglobulin κ Locus." Bio/Technology, 11:911-914 (1993).
Deng, C. et al., "Reexamination of Gene Targeting Frequency as a Function of the Extent of Homology Between the Targeting Vector and the Target Focus," Mol. Cell. Biol. 12(8):3365-3371 (1992).
Devoy, A. et al., "Genomically Humanized Mice: Technologies and Promises," Nature, 13:14-20 (2012).
Doetschman et al., "'Targeted Correction of a Mutant HPRT Gene in Mouse Embryonic Stem Cells," Nature 330:576-578 (1987).
Durdik, J. et al., "Isotype Switching by a Microinjected mu Immunoglobulin Heavy Chain Gene in Transgenic Mice," Proc. Natl. Acad. Sci. USA 86(7):2346-2350 (1989).
Duthell, N. et al., "Characterization of the mouse Adeno-associated virus AAVS1 ortholog." J. Virol. 78(16):8917-21 (2004).
Endrizzi, M.G. et al., "Genomic sequence analysis of the mouse Naip gene array," Genome Res., 10(8):1095-102 (2000).
Fan, Y. et al., "Gene content and function of the ancestral chromosome fusion site in human chromosome 2q13-2q14.1 and paralogous regions," Genome Res., 12(11):1663-72 (2002).

(56) References Cited

OTHER PUBLICATIONS

Feng, Y.Q. et al., "Site-specific Chromosomal Integration in Mammalian Cells: Highly Efficient CRE Recombinase-mediated Cassette Exchange," J. Mol. Biol., 292:779-785 (1999).
Fenske, D.B. et al., "Long-curculating vectors for the systemic delivery of genes," Curr Opin Mol Ther, 3(2):153-8 (2001).
Fishwild, D.M. et al., "High-Avidity Human IgG kappa Monoclonal Antibodies From a Novel Strain of Minilocus Transgenic Mice," Nat. Biotechnol. 14(7):845-851 (1996).
Foord, O.S. et al., "Long-Distance PCR," PCR Methods Appl. 3(6):S149-S161 (1994).
Forozan, F. et al., "Genome Screening by Comparative Genomic Hybridization," Trends Genet. 13(10:405-409 (1997).
Frengen, E. et al., "Modular Bacterial Artificial Chromosome Vectors for Transfer of Large Inserts into Mammalian Cells," Genomics, 68:118-126 (2000).
Fujieda et al., "Multiple Types of Chimeric Germline Ig Heavy Chain Transcripts in Human B Cells," J Immunol 157(8):3450-3459 (1996).
Fujieda, S. et al., "Direct evidence that gamma 1 and gamma 3 switching in human B cells is interleukin-10 dependent," Mol Immunol., 33(17-18):1335-43 (1996).
Gerstein, R.M. et al., "Isotype Switching of an Immunoglobulin Heavy Chain Transgene Occurs by DNA Recombination Between Different Chromosomes," Cell, 63(3):537-548 (1990).
Gu, H. et al., "Independent Control of Immunoglobulin Switch Recombination at Individual Switch Regions Evidenced through Cre-loxP-Mediated Gene Targeting," Cell, 73:1155-1164 (1993).
Haines and Brodeur, "Accessibility Changes Across the Mouse IgH-V Locus During B Cell Development," EurJ Immunol 28:4228-4235 (1998).
Hall, S.D. et al., "Homologous Pairing and Strand Exchange Promoted by the *Escherichia coli* RecT protein," Proc Natl Acad Sci USA 91:3205-3209 (1994).
Hall et al., "Identification and Characterization of the *Escherichia coli* RecT Protein, a Protein Encoded by the recE Region that Promotes Renaturation of Homologous Single-Stranded DNA," Journal of Bacteriology 175(4):277-287 (1993).
Hammer, R.E. et al., "Genetic Engineering of Mammalian Embryos," J. Anim. Sci., 63(1):269-78 (1986).
Hammer, R.E. et al., "Spontaneous Inflammatory Disease in Transgenic Rats Expressing HLA-B27 and Human B2m: An animal model of HLA-B27-associated Human Disorders," Cell, 63(5):1099-112 (1990).
Herault, Y. et al., "Engineering Chromosomes in Mice Through Targeting Meiotic Recombination (TAMERE)," Nat. Genet., 20(4):381-384 (1998).
Hill, F. et al., "BAC Trimming: Minimizing Clone Overlaps," Genomics, 64(1):111-113 (2000).
Hochepied, T. et al., "Breaking the Species Barrier: Deprivation of Germline-Competent Embryonic Stem Cells from Musspretus x C57BL/6 Hybrids," Stem Cells, 22(4):441-447 (2004).
Hoess et al., "The Role of the loxP Spacer Region in P1 Site-Specific Recombination," Nucleic Acids Research 14(5):2287-2300 (1986).
Houldsworth, J. et al., "Comparative Genomic Hybridization: An Overview," Am. J. Pathol. 145(6): 1253-1260 (1994).
Jacks, T. et al., "Effects of an Rb mutation in the Mouse," Nature, 359:295-300 (1992).
Jaenisch, R. et al., "Transgenic animals," Science, 240(4858):1468-74 (1988).
Jakobovits, A. et al., "Production of Transgenic Mice with Yeast Artificial Chromosomes," Methods in Molecular Biology, 136:435-453 (2000).
Jakobovits, A., "Humanizing the Mouse Genome," Current Biology, 4(8):761-763 (1994).
Jensen, M. et al., "One Step Generation of Fully Chimeric Antibodies Using Cgamma1- and C kappa Mutant Mice," J. Immunother., 30(3):338-349 (2007).
Jessen, J.R. et al., "Modification of Bacterial Artificial Chromosomes Through Chi-stimulated Homologous Recombination and its Application in Zebrafish Transgenesis," Proc. Natl. Acad. Sci, USA, 95:5121-5126 (1998).
Joyner, "Gene Targeting: A Practical Approach," (2005).
Kawasaki, K. et al., "One-Megabase Sequence Analysis of the Human Immunoglobulin λ Gene Locus," Genome Research, 7:250-261 (1997).
Kohler and Milstein, "Continuous cultures of fused cells secreting antibody of predefined specificity," Nature 256:495-497 (1975).
Kolb, A.F. et al., "Insertion of a Foreign Gene into the β-casein Locus by Cre-mediated Site-Specific Recombination," Gene, 227:21-31 (1999).
Kolb, A.F. et al., "Selection-marker-free modification of the murine beta-casein gene using a lox2272 [correction of 1ox2722) site," Anal Biochem, 290(2):260-71 (2001).
Koller et al., "Germ-Line Transmission of a Planned Alteration Made in a Hypoxanthine Phosphoribosyltransferase Gene by Homologous Recombination in Embryonic Stem Cells," Proc Natl Acad Sci USA 86:8927-8931 (1989).
Kolodner et al., "Homologous Pairing Proteins Encoded by the *Escherichia coli* recE and recT Genes," Molecular Microbiology 11(1):23-30 (1994).
Kovali and Matthews, "Toroidal Structure of Lambda-Exonuclease," Science 277(5333):1824-1927 (1997).
Kuehn, M.R. et al., "A potential animal model for Lesch-Nyham syndrome through introduction of HPRT mutations into mice," Nature, 326(6110):295-8 (1987).
Kuhn et al., "Generation and Analysis of Interleukin-4 Deficient Mice," Science 254(5032):707-710 (1991).
Kusano et al., "Involvement of RecE Exonuclease and RecT annealing protein in DNA Double-Strand Break Repair by Homologous Recombination," Gene 138:17-25 (1994).
Laan, M et al., "Solid-Phase Minisequencing Confirmed by FISH Analysis in Determination of Gene Copy Number," Hum. Genet. 96(3):275-280 (1995).
Lee, Y. et al., "Cross-referencing eukaryotic genomes: TIGR Orthologous Genes Alignments (TOGA)," Genome Res., 12(3):493-502 (2002).
Lefranc, M.-P., "Nomenclature of the Human Immunoglobulin Heavy (IGH) Genes," Exp. Clin. Immunogenet., 18:100-116 (2001).
Lefranc, M.-P., "Nomenclature of the Human Immunoglobulin Lambda (IGL) Genes," Exp. Clin. Immunogenet., 18:242-254 (2001).
Lie, Y.S. et al., "Advances in Quantitative PCR Technology: 5' Nuclease Assays," Curr. Opin. Biotechnol., 9(1):43-48 (1998).
Lizardi, P.M. et al., "Mutation Detection and Single-molecule Counting Using Isothermal Rolling Circle Amplification," Nat. Genet. 19(3):225-232 (1998).
Matsuda, F. et al., "Structure and physical map of 64 variable segments in the 3'0.8-megabase region of the human immunoglobulin heavy-chain locus," Nat Genet., 3(1):88-94 (1993).
Matsuda, F. et al., "The Complete Nucleotide Sequence of the Human Immunoglobulin Heavy Chain Variable Region Locus," J. Exp. Med. 188(11):2151-2162 (1998).
Mendez, M.J. et al., "Functional Transplant of Megabase Human Immunoglobulin Loci Recapitulates Human Antibody Response in Mice," Nature Genetics, 15:146-156 (1997).
Metzger et al., "Conditional site-specific recombination in mammalian cells using a ligand-dependent chimeric Cre recombinase," Proc Natl Acad Sci USA 92(15):6991-6995 (1995).
Meyer-Leon et al., "Site-specific genetic recombination promoted by the FLP protein of the yeast 2-micron plasmid in vitro," Cold Spring Harb Symp Quant Biol 49:797-804 (1984).
Mitra, R.D. et al., "In Situ Localized Amplification and Contact Replication of Many Individual DNA Molecules," Nucleic Acids Res., 27(24):e34 (1999).
Moens, C.B. et al., "Defects in heart and lung development in compound heterozygotes for two different targeted mutations at the N-myc locus," Development, 119(2):485-99 (1993).
Monaco, A.P. et al., "YACs, BACs, PACs and MACs: Artificial Chromosomes as Research Tools," TIBTECH, 12:280-286 (1994).

(56) References Cited

OTHER PUBLICATIONS

Moreadith et al., "Gene targeting in embryonic stem cells: the new physiology and metabolism," J. Mol. Med. 75(3):208-216 (1997).
Morrow, B. et al., "Gene Targeting in mammalian cells by homologous recombination," Curr Opin Biotechnol, 4(5):577-82 (1993).
Mullins, L.J. et al., "Transgenesis in the rat and larger mammals," J. Clin. Invest. 97:1557-1560 (1996).
Murphy, K.C. et al., "Lambda Gam protein inhibits the helicase and chi-stimulated recombination activities of Escherichia coli RecBCD enzyme," J. Bacteriol. 173(18):5808-21 (1991).
Muyrers, J.P. et al., "Rapid Modification of Bacterial Artificial Chromosomes by ET-Recombination," Nucleic Acids Res., 27(6):1555-1557 (1999).
Myers, R.S. et al., "Chi and the RecBC D enzyme of Escherichia coli," Annu Rev Genet., 28:49-70 (1994).
Müller, U., "Ten Years of Gene Targeting: Targeted Mouse Mutants, from Vector Design to Phenotype Analysis," Mech. of Dev., 82:3-21 (1999).
Narayanan, K. et al., "Efficient and Precise Engineering of a 200 kb β-globin Human/Bacterial Artificial Chromosome in E. coli DH10B Using An Inducible Homologous Recombination System," Gene Therapy, 6:442-447 (1999).
Neuberger, M.S. et al., "Isotype Exclusion and Transgene Down-Regulation in Immunoglobulin-∧Transgenic Mice," Nature 338:350-352 (1989).
Noirot and Kolodner, "DNA Strand Invasion Promoted by Escherichia coli RecT Protein," J Biol Chem 273(20):12274:12280 (1998).
Ong et al., "3' IgH Enhancer Elements Shift Synergistic Interactions During B Cell Development," J Immunol. 160:4896-4903 (1998).
Osoegawa, K. et al., "An Improved Approach for Construction of Bacterial Artificial Chromosome Libraries," Genomics, 52:1-8 (1998).
Osoegawa, K. et al., "Bacterial artificial chromosome libraries for mouse sequencing and functional analysis," Genome Res., 10(1):116-28 (2000).
Pan, Q. et al., "Regulation of the Promoter for Human Immunoglobulin Lambda3 Germ-Line Transcription and its Interaction with the 3'Alpha Enhancer," Eur J Immunol 39:1019-1029 (2000).
Pera et al., "Human Embryonic Stem Cells," Journal of Cell Science 113:5-10 (2000).
Peters, T. et al., "Organization of mouse Iroguois homeobox genes in two clusters suggests a conserved regulation and function in vertebrate development," Genome Res., 10(10):1453-62 (2000).
Platt, J.L. et al., "New directions for organ transplantation," Nature, 392(6679 Suppl.) 11-7 (1998).
Ponce, M.R. et al., "PCR Amplification of Long DNA Fragments," Nucleic Acids Res., 20(3):623 (1992).
Popov, A.V. et al., "Assembly and extension of yeast artificial chromosomes to build up a large locus," Gene, 1779102):195-201 (1996).
Poteete et al., "Modulation of Escherichia coli RecBCD Activity by the Bacteriophage Lambda Gam and P22 Abc Functions," Journal of Bacteriology 170(5):2012-2021 (1988).
Ronai, D. et al., "Variegated Expression of the Endogenous Immunoglobulin Heavy-Chain Gene in the Absence of the Intronic Locus Control Region," Mol. Cell. Biol., 19(10):7031-7039 (1999).
Schlake, T. et al., "Use of Mutated FLP Recognition Target (FRT) Sites for the Exchange of Expression Cassettes at Defined Chromosomal Loci," Biochemistry, 33:12746-12751 (1994).
Schoonjans, L. et al., "Improved Generation of Germline-Competent Embryonic Stem Cell Lines from Inbred Mouse Strains," Stem Cells, 21(1):90-97 (2003).
Schwartzberg et al., "Germ-Line Transmission of a c-abl Mutation Produced by Targeted Gene Disruption in ES Cells," Reports 799-803 (1989).
Scott, C.T., "Mice with a Human Touch," Nat. Biotech., 25(10):1075-1077 (2007).
Shi, Y.-P. et al., "The Mapping of Transgenes by Fluorescence in situ Hybridization on G-banded Mouse Chromosomes," Mammalian Genome, 5:337-341 (1994).
Shizuya, H. et al., "Cloning and Stable Maintenance of 300-kilobase-pair Fragments of Human DNA in Escherichia coli using an F-factor-based Vector," Proc. Natl. Acad. Sci. USA, 89:8794-8797 (1992).
Smith, D.R. et al., "Genomic Analysis of Transgenic Animals," Methods Mol. Biol. 18:323-327 (1993).
Smithies, O. et al., "Insertion of DNA Sequences into the Human Chromosomal Beta-Globin Locus by Homologous Recombination," Nature, 317(6034):230-234 (2007).
Soukharev, S. et al., "Segmental Genomic Replacement in Embryonic Stem Cells by Double lox Targeting," Nucleic Acids Res., 27(18):e21 (1999).
Spanopoulou et al., "'Functional immunoglobulin transgenes guide ordered B-cell differentiation in Rag-1-deficient mice," Genes Dev 8(9):1030-1042 (1994).
Spazierer, D. et al., "Epiplakin gene analysis in mouse reveals a single exon encoding a 725-kDa protein with expression restricted to epithelial tissues," J Biol Chem., 278(34):31657-66 (2003).
Takada, S. et al., "Construction of Chimaeric Processed Immunoglobulin Genes Containing Mouse Variable and Human Constant Region Sequences," Nature, 314:452-454 (1985).
Taki, S. et al., "Targeted Insertion of a Variable Region Gene into the Immunoglobulin Heavy Chain Locus," Science, 262:1268-1271 (1993).
Tan, W. et al., "Molecular Beacons: a Novel DNA Probe for Nucleic Acid and Protein Studies," Eur. J. Chem., 6(7):1107-1111 (2000).
Tao, Q. et al., "Cloning and stable maintenance of DNA fragments over 300 kb in Escherichia coli with conventional plasmid-based vectors," Nucleic Acids Res., 26(21):4901-9 (1998).
Tatusov, R.L. et al., "A genomic perspective on protein families," Science, 278(5338):631-7 (1997).
Taylor, L.D., "Human Immunoglobulin Transgenes Undergo Rearrangement, Somatic Mutation and Class Switching in Mice That Lock Endogenous IgM," Int. Immunol. 6(4):579-591 (1994).
Thomas, K.R. et al., "Site-directed Mutagenesis by Gene Targeting in Mouse Embryo-Derived Stem Cells," Cell, 51(3):503-512 (1987).
Thomas, K.R. et al., "Targeted disruption of the murine int-1 proto-oncogene resulting in severe abnormalities in midbrain and cerebellar development," Nature, 346(6287):847-50 (1990).
Thompson et al., "Germline transmission and expression of a corrected HPRT gene produced by gene targeting in embryonic stem cells," Cell 56(2):313-321 (1989).
Thompson, C.T et al., "Cytogenetic Profiling Using Fluorescence in Situ Hybridization (FISH) and Comparative Genomic Hybridization (CGH)," J. Cell. Biochem. Suppl., 17G:139-143 (1993).
Thresher et al., "Electron Microscopic Visualization of RecT Protein and its Complexes with DNA," J Mol Biol 254:364-371 (1995).
Thykjaer, T. et al., "Gene Targeting Approaches Using Positive-negative Selection and Large Flanking Regions," Plant Molecular Biology, 35:523-530 (1997).
Tomizuka, K. et al., "Double Trans-Chromosomic Mice: Maintenance of Two Individual Human Chromosome Fragments Containing Ig Heavy and Kappa Loci and Expression of Fully Human Antibodies," Proc. Natl. Acad. Sci. USA., 97(2):722-727 (2000).
Valenzuela, D.M. et al., "High-throughput Engineering of the Mouse Genome Couples with High-Resolution Expression Analysis," Nature Biotechnology, 21(6):652-659 (2003).
Wall, R.J. et al., "Pronuclear microinjection," Cloning Stem Cells, 3(4):209-20 (2001).
Waterhouse, P. et al., "Combinatorial Infection and In Vivo Recombination: A strategy for Making Large Phage Antibody Repertoires," Nucleic Acids Research, 21(9):2265-2266 (1993).
Waterson et al., "Initial sequencing and comparative analysis of the mouse genome," Nature 420:520-562 (2002).
Wilke, K. et al., "Diagnosis of Haploidy and Triploidy Based on Measurement of Gene Copy Number by Real-Time PCR," Human Mutation 16:431-436 (2000).

(56) References Cited

OTHER PUBLICATIONS

Willers et al., "Apparent Trans-Chromosomal Antibody Class Switch in Mice Bearing an Igh(a) mu-Chain Transgene on an Igh(b) Genetic Background," Immunobiol 200(1):150-164 (1999).

Yang et al., "Fully human anti-interleukin-8 monoclonal antibodies: potential therapeutics for the treatment of inflammatory disease states," Journal of Leukocyte Biology 66(3):401-410 (1999).

Yang, X.W. et al., "Homologous Recombination Based Modification in *Escherichia coli* and Germline Transmission in Transgenic Mice of a Bacterial Artificial Chromosome," Nature Biotechnology, 15:859-865 (1997).

Yu, D. et al., "An Efficient Recombination System for Chromosome Engineering in *Escherichia coli*," Proc. Natl. Acad. Sci. USA, 97(11):5978-5983 (2000).

Zhang, Y. et al., "A New Logic for DNA Engineering Using Recombination in *Escherichia coli*," Nat. Genet., 20(2):123-128 (1998).

Zou, R.-Y. et al., "Cre-loxP-Mediated Gene Replacement: A Mouse Strain Producing Humanized Antibodies," Current Biology, 4:1099-1103 (1994).

\* cited by examiner

FIGURE 3A

```
              10         20         30         40         50         60
         CCCCGGGCTT CCTGTTCTAA TAAGAATACC TCCTAGGTCC CCCATGGGCT AACCTCATCT
         GGGGCCCGAA GGACAAGATT ATTCTTATGG AGGATCCAGG GGGTACCCGA TTGGAGTAGA 70         80         90        100        110        120
         TTGGTACTCA ACAGGGGTCT TCTTTATGAG CTTCGGACCA GCTCTTTTGA TGTGGCAGGG
         AACCATGAGT TGTCCCCAGA AGAAATACTC GAAGCCTGGT CGAGAAAACT ACACCGTCCC 130        140        150        160        170        180
         ACTGACCCTG GGTGGGGAAG CCACTCAGTG CATGACCCCA GCTGGTTCAC CACATATACC
         TGACTGGGAC CCACCCCTTC GGTGAGTCAC GTACTGGGGT CGACCAAGTG GTGTATATGG 190        200        210        220        230
         ACATACTTTT CTTGCAGGTC TGGGACACAG C ATG CCC CGG GGC CCA GTG GCT GCC
         TGTATGAAAA GAACGTCCAG ACCCTGTGTC G TAC GGG GCC CCG GGT CAC CGA CGG
                                           Met Pro Arg Gly Pro Val Ala Ala>

240        250        260        270        280
         TTA CTC CTG CTG ATT CTC CAT GGA GCT TGG AGC TGC CTG GAC CTC ACT
         AAT GAG GAC GAC TAA GAG GTA CCT CGA ACC TCG ACG GAC CTG GAG TGA
         Leu Leu Leu Leu Ile Leu His Gly Ala Trp Ser Cys Leu Asp Leu Thr>

290        300        310        320        330
         TGC TAC ACT GAC TAC CTC TGG ACC ATC ACC TGT GTC CTG GAG ACA CGG
         ACG ATG TGA CTG ATG GAG ACC TGG TAG TGG ACA CAG GAC CTC TGT GCC
         Cys Tyr Thr Asp Tyr Leu Trp Thr Ile Thr Cys Val Leu Glu Thr Arg>

340        350        360        370
         AGC CCC AAC CCC AGC ATA CTC AGT CTC ACC TGG CAA GAT GAA TAT GAG
         TCG GGG TTG GGG TCG TAT GAG TCA GAG TGG ACC GTT CTA CTT ATA CTC
         Ser Pro Asn Pro Ser Ile Leu Ser Leu Thr Trp Gln Asp Glu Tyr Glu>

380        390        400        410        420
         GAA CTT CAG GAC CAA GAG ACC TTC TGC AGC CTA CAC AAG TCT GGC CAC
         CTT GAA GTC CTG GTT CTC TGG AAG ACG TCG GAT GTG TTC AGA CCG GTG
         Glu Leu Gln Asp Gln Glu Thr Phe Cys Ser Leu His Lys Ser Gly His>

430        440        450        460        470
         AAC ACC ACA CAT ATA TGG TAC ACG TGC CAT ATG CGC TTG TCT CAA TTC
         TTG TGG TGT GTA TAT ACC ATG TGC ACG GTA TAC GCG AAC AGA GTT AAG
         Asn Thr Thr His Ile Trp Tyr Thr Cys His Met Arg Leu Ser Gln Phe>

480        490        500        510        520
         CTG TCC GAT GAA GTT TTC ATT GTC AAC GTG ACG GAC CAG TCT GGC AAC
         GAC AGG CTA CTT CAA AAG TAA CAG TTG CAC TGC CTG GTC AGA CCG TTG
         Leu Ser Asp Glu Val Phe Ile Val Asn Val Thr Asp Gln Ser Gly Asn>

530        540        550        560        570
         AAC TCC CAA GAG TGT GGC AGC TTT GTC CTG GCT GAG AGC ATC AAG CCA
         TTG AGG GTT CTC ACA CCG TCG AAA CAG GAC CGA CTC TCG TAG TTC GGT
         Asn Ser Gln Glu Cys Gly Ser Phe Val Leu Ala Glu Ser Ile Lys Pro>
```

FIGURE 3B

```
       580            590            600            610
 GCT CCC CCC TTG AAC GTG ACT GTG GCC TTC TCA GGA CGC TAT GAT ATC
 CGA GGG GGG AAC TTG CAC TGA CAC CGG AAG AGT CCT GCG ATA CTA TAG
 Ala Pro Pro Leu Asn Val Thr Val Ala Phe Ser Gly Arg Tyr Asp Ile>

620            630            640            650            660
  TCC TGG GAC TCA GCT TAT GAC GAA CCC TCC AAC TAC GTG CTG AGA GGC
  AGG ACC CTG AGT CGA ATA CTG CTT GGG AGG TTG ATG CAC GAC TCT CCG
  Ser Trp Asp Ser Ala Tyr Asp Glu Pro Ser Asn Tyr Val Leu Arg Gly>

670            680            690            700            710
   AAG CTA CAA TAT GAG CTG CAG TAT CGG AAC CTC AGA GAC CCC TAT GCT
   TTC GAT GTT ATA CTC GAC GTC ATA GCC TTG GAG TCT CTG GGG ATA CGA
   Lys Leu Gln Tyr Glu Leu Gln Tyr Arg Asn Leu Arg Asp Pro Tyr Ala>

720            730            740            750            760
      GTG AGG CCG GTG ACC AAG CTG ATC TCA GTG GAC TCA AGA AAC GTC TCT
      CAC TCC GGC CAC TGG TTC GAC TAG AGT CAC CTG AGT TCT TTG CAG AGA
      Val Arg Pro Val Thr Lys Leu Ile Ser Val Asp Ser Arg Asn Val Ser>

770            780            790            800            810
         CTT CTC CCT GAA GAG TTC CAC AAA GAT TCT AGC TAC CAG CTG CAG ATG
         GAA GAG GGA CTT CTC AAG GTG TTT CTA AGA TCG ATG GTC GAC GTC TAC
         Leu Leu Pro Glu Glu Phe His Lys Asp Ser Ser Tyr Gln Leu Gln Met>

820            830            840            850
            CGG GCA GCG CCT CAG CCA GGC ACT TCA TTC AGG GGG ACC TGG AGT GAG
            GCC CGT CGC GGA GTC GGT CCG TGA AGT AAG TCC CCC TGG ACC TCA CTC
            Arg Ala Ala Pro Gln Pro Gly Thr Ser Phe Arg Gly Thr Trp Ser Glu>

860            870            880            890            900
   TGG AGT GAC CCC GTC ATC TTT CAG ACC CAG GCT GGG GAG CCC GAG GCA
   ACC TCA CTG GGG CAG TAG AAA GTC TGG GTC CGA CCC CTC GGG CTC CGT
   Trp Ser Asp Pro Val Ile Phe Gln Thr Gln Ala Gly Glu Pro Glu Ala>

910            920            930            940            950
      GGC TGG GAC CCT CAC ATG CTG CTG CTC CTG GCT GTC TTG ATC ATT GTC
      CCG ACC CTG GGA GTG TAC GAC GAC GAG GAC CGA CAG AAC TAG TAA CAG
      Gly Trp Asp Pro His Met Leu Leu Leu Leu Ala Val Leu Ile Ile Val>

960            970            980            990            1000
         CTG GTT TTC ATG GGT CTG AAG ATC CAC CTG CCT TGG AGG CTA TGG AAA
         GAC CAA AAG TAC CCA GAC TTC TAG GTG GAC GGA ACC TCC GAT ACC TTT
         Leu Val Phe Met Gly Leu Lys Ile His Leu Pro Trp Arg Leu Trp Lys>

1010            1020            1030            1040            1050
            AAG ATA TGG GCA CCA GTG CCC ACC CCT GAG AGT TTC TTC CAG CCC CTG
            TTC TAT ACC CGT GGT CAC GGG TGG GGA CTC TCA AAG AAG GTC GGG GAC
            Lys Ile Trp Ala Pro Val Pro Thr Pro Glu Ser Phe Phe Gln Pro Leu>
```

FIGURE 3C

```
        1060           1070           1080           1090
  TAC AGG GAG CAC AGC GGG AAC TTC AAG AAA TGG GTT AAT ACC CCT TTC
  ATG TCC CTC GTG TCG CCC TTG AAG TTC TTT ACC CAA TTA TGG GGA AAG
  Tyr Arg Glu His Ser Gly Asn Phe Lys Lys Trp Val Asn Thr Pro Phe>

1100           1110           1120           1130           1140
  ACG GCC TCC AGC ATA GAG TTG GTG CCA CAG AGT TCC ACA ACA ACA TCA
  TGC CGG AGG TCG TAT CTC AAC CAC GGT GTC TCA AGG TGT TGT TGT AGT
  Thr Ala Ser Ser Ile Glu Leu Val Pro Gln Ser Ser Thr Thr Thr Ser>

1150           1160           1170           1180           1190
  GCC TTA CAT CTG TCA TTG TAT CCA GCC AAG GAG AAG AAG TTC CCG GGG
  CGG AAT GTA GAC AGT AAC ATA GGT CGG TTC CTC TTC TTC AAG GGC CCC
  Ala Leu His Leu Ser Leu Tyr Pro Ala Lys Glu Lys Lys Phe Pro Gly>

1200           1210           1220           1230           1240
  CTG CCG GGT CTG GAA GAG CAA CTG GAG TGT GAT GGA ATG TCT GAG CCT
  GAC GGC CCA GAC CTT CTC GTT GAC CTC ACA CTA CCT TAC AGA CTC GGA
  Leu Pro Gly Leu Glu Glu Gln Leu Glu Cys Asp Gly Met Ser Glu Pro>

1250           1260           1270           1280           1290
  GGT CAC TGG TGC ATA ATC CCC TTG GCA GCT GGC CAA GCG GTC TCA GCC
  CCA GTG ACC ACG TAT TAG GGG AAC CGT CGA CCG GTT CGC CAG AGT CGG
  Gly His Trp Cys Ile Ile Pro Leu Ala Ala Gly Gln Ala Val Ser Ala>

1300           1310           1320           1330
  TAC AGT GAG GAG AGA GAC CGG CCA TAT GGT CTG GTG TCC ATT GAC ACA
  ATG TCA CTC CTC TCT CTG GCC GGT ATA CCA GAC CAC AGG TAA CTG TGT
  Tyr Ser Glu Glu Arg Asp Arg Pro Tyr Gly Leu Val Ser Ile Asp Thr>

1340           1350           1360           1370           1380
  GTG ACT GTG GGA GAT GCA GAG GGC CTG TGT GTC TGG CCC TGT AGC TGT
  CAC TGA CAC CCT CTA CGT CTC CCG GAC ACA CAG ACC GGG ACA TCG ACA
  Val Thr Val Gly Asp Ala Glu Gly Leu Cys Val Trp Pro Cys Ser Cys>

1390           1400           1410           1420           1430
  GAG GAT GAT GGC TAT CCA GCC ATG AAC CTG GAT GCT GGC AGA GAG TCT
  CTC CTA CTA CCG ATA GGT CGG TAC TTG GAC CTA CGA CCG TCT CTC AGA
  Glu Asp Asp Gly Tyr Pro Ala Met Asn Leu Asp Ala Gly Arg Glu Ser>

1440           1450           1460           1470           1480
  GGT CCT AAT TCA GAG GAT CTG CTC TTG GTC ACA GAC CCT GCT TTT CTG
  CCA GGA TTA AGT CTC CTA GAC GAG AAC CAG TGT CTG GGA CGA AAA GAC
  Gly Pro Asn Ser Glu Asp Leu Leu Leu Val Thr Asp Pro Ala Phe Leu>

1490           1500           1510           1520           1530
  TCT TGT GGC TGT GTC TCA GGT AGT GGT CTC AGG CTT GGG GGC TCC CCA
  AGA ACA CCG ACA CAG AGT CCA TCA CCA GAG TCC GAA CCC CCG AGG GGT
  Ser Cys Gly Cys Val Ser Gly Ser Gly Leu Arg Leu Gly Gly Ser Pro>
```

Figure 3D

```
         1540           1550           1560           1570
   GGC AGC CTA CTG GAC AGG TTG AGG CTG TCA TTT GCA AAG GAA GGG GAC
   CCG TCG GAT GAC CTG TCC AAC TCC GAC AGT AAA CGT TTC CTT CCC CTG
   Gly Ser Leu Leu Asp Arg Leu Arg Leu Ser Phe Ala Lys Glu Gly Asp>

1580         1590           1600           1610           1620
   TGG ACA GCA GAC CCA ACC TGG AGA ACT GGG TCC CCA GGA GGG GGC TCT
   ACC TGT CGT CTG GGT TGG ACC TCT TGA CCC AGG GGT CCT CCC CCG AGA
   Trp Thr Ala Asp Pro Thr Trp Arg Thr Gly Ser Pro Gly Gly Gly Ser>

1630           1640           1650           1660           1670
   GAG AGT GAA GCA GGT TCC CCC CCT GGT CTG GAC ATG GAC ACA TTT GAC
   CTC TCA CTT CGT CCA AGG GGG GGA CCA GAC CTG TAC CTG TGT AAA CTG
   Glu Ser Glu Ala Gly Ser Pro Pro Gly Leu Asp Met Asp Thr Phe Asp>

1680           1690           1700           1710           1720
   AGT GGC TTT GCA GGT TCA GAC TGT GGC AGC CCC GTG GAG ACT GAT GAA
   TCA CCG AAA CGT CCA AGT CTG ACA CCG TCG GGG CAC CTC TGA CTA CTT
   Ser Gly Phe Ala Gly Ser Asp Cys Gly Ser Pro Val Glu Thr Asp Glu>

1730           1740           1750           1760           1770
   GGA CCC CCT CGA AGC TAT CTC CGC CAG TGG GTG GTC AGG ACC CCT CCA
   CCT GGG GGA GCT TCG ATA GAG GCG GTC ACC CAC CAG TCC TGG GGA GGT
   Gly Pro Pro Arg Ser Tyr Leu Arg Gln Trp Val Val Arg Thr Pro Pro>

1780           1790           1800
   CCT GTG GAC AGT GGA GCC CAG AGC AGC TAG
   GGA CAC CTG TCA CCT CGG GTC TCG TCG ATC
   Pro Val Asp Ser Gly Ala Gln Ser Ser ***>
```

METHOD FOR DETECTING THE REPLACEMENT OF AN ENDOGENOUS ALLELE WITH A MODIFIED ALLELE BY HOMOLOGOUS RECOMBINATION IN A MOUSE ES CELL

This application is a continuation of U.S. patent application Ser. No. 11/809,473, filed 1 Jun. 2007, which is a continuation of U.S. patent application Ser. No. 10/415,440, filed 29 Apr. 2003, which is National Stage of International Application No. PCT/US01/45375, filed 31 Oct. 2001 and published in English under PCT Article 21(2), which claims the benefit of U.S. patent application Ser. No. 09/732,234, filed 7 Dec. 2000, which is now U.S. Pat. No. 6,586,251, which claims the benefit of U.S. Provisional Application No. 60/244,665, filed 31 Oct. 2000, which applications are herein incorporated by reference. Throughout this application various publications are referenced. The disclosures of these publications in their entireties are hereby incorporated by reference into this application.

FIELD OF THE INVENTION

The field of this invention is a method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. The field of the invention further provides for a rapid and convenient method of detecting eukaryotic cells in which the LTVEC has correctly targeted and modified the desired endogenous gene(s) or chromosomal locus (loci). The field also encompasses the use of these cells to generate organisms bearing the genetic modification, the organisms, themselves, and methods of use thereof.

INTRODUCTION

The use of LTVECs provides substantial advantages over current methods. For example, since these are derived from DNA fragments larger than those currently used to generate targeting vectors, LTVECs can be more rapidly and conveniently generated from available libraries of large genomic DNA fragments (such as BAC and PAC libraries) than targeting vectors made using current technologies. In addition, larger modifications as well as modifications spanning larger genomic regions can be more conveniently generated than using current technologies.

Furthermore, the present invention takes advantage of long regions of homology to increase the targeting frequency of "hard to target" loci, and also diminishes the benefit, if any, of using isogenic DNA in these targeting vectors.

The present invention thus provides for a rapid, convenient, and streamlined method for systematically modifying virtually all the endogenous genes and chromosomal loci of a given organism.

BACKGROUND OF THE INVENTION

Gene targeting by means of homologous recombination between homologous exogenous DNA and endogenous chromosomal sequences has proven to be an extremely valuable way to create deletions, insertions, design mutations, correct gene mutations, introduce transgenes, or make other genetic modifications in mice. Current methods involve using standard targeting vectors, with regions of homology to endogenous DNA typically totaling less than 10-20 kb, to introduce the desired genetic modification into mouse embryonic stem (ES) cells, followed by the injection of the altered ES cells into mouse embryos to transmit these engineered genetic modifications into the mouse germline (Smithies et al., Nature, 317:230-234, 1985; Thomas et al., Cell, 51:503-512, 1987; Koller et al., Proc Natl Acad Sci USA, 86:8927-8931, 1989; Kuhn et al., Science, 254:707-710, 1991; Thomas et al., Nature, 346:847-850, 1990; Schwartzberg et al., Science, 246:799-803, 1989; Doetschman et al., Nature, 330:576-578, 1987; Thomson et al., Cell, 5:313-321, 1989; DeChiara et al., Nature, 345:78-80, 1990; U.S. Pat. No. 5,789,215, issued Aug. 4, 1998 in the name of GenPharm International) In these current methods, detecting the rare ES cells in which the standard targeting vectors have correctly targeted and modified the desired endogenous gene(s) or chromosomal locus(loci) requires sequence information outside of the homologous targeting sequences contained within the targeting vector. Assays for successful targeting involve standard Southern blotting or long PCR (Cheng, et al., Nature, 369:684-5, 1994; Foord and Rose, PCR Methods Appl, 3:S149-61, 1994; Ponce and Micol, Nucleic Acids Res, 20:623, 1992; U.S. Pat. No. 5,436,149 issued to Takara Shuzo Co., Ltd.) from sequences outside the targeting vector and spanning an entire homology arm (see Definitions); thus, because of size considerations that limit these methods, the size of the homology arms are restricted to less than 10-20 kb in total (Joyner, The Practical Approach Series, 293, 1999).

The ability to utilize targeting vectors with homology arms larger than those used in current methods would be extremely valuable. For example, such targeting vectors could be more rapidly and conveniently generated from available libraries containing large genomic inserts (e.g. BAC or PAC libraries) than targeting vectors made using current technologies, in which such genomic inserts have to be extensively characterized and trimmed prior to use. In addition, larger modifications as well as modifications spanning larger genomic regions could be more conveniently generated and in fewer steps than using current technologies. Furthermore, the use of long regions of homology could increase the targeting frequency of "hard to target" loci in eukaryotic cells, since the targeting of homologous recombination in eukaryotic cells appears to be related to the total homology contained within the targeting vector (Deng and Capecchi, Mol Cell Biol, 12:3365-71, 1992). In addition, the increased targeting frequency obtained using long homology arms could diminish any potential benefit that can be derived from using isogenic DNA in these targeting vectors.

The problem of engineering precise modifications into very large genomic fragments, such as those cloned in BAC libraries, has largely been solved through the use of homologous recombination in bacteria (Zhang, et al., Nat Genet, 20:123-8, 1998; Yang, et al., Nat Biotechnol, 15:859-65, 1997; Angrand, et al., Nucleic Acids Res, 27:e16, 1999; Muyrers, et al., Nucleic Acids Res, 27:1555-7, 1999; Narayanan, et al., Gene Ther, 6:442-7, 1999), allowing for the construction of vectors containing large regions of homology to eukaryotic endogenous genes or chromosomal loci. However, once made, these vectors have not been generally useful for modifying endogenous genes or chromosomal loci via homologous recombination because of the difficulty in detecting rare correct targeting events when homology arms are larger than 10-20 kb (Joyner, The Practical Approach Series, 293, 1999). Consequently, vectors generated using bacterial homologous recombination from BAC genomic fragments must still be extensively trimmed prior to use as targeting vectors (Hill et al., Genomics, 64:111-3, 2000). Therefore, there is still a need for a rapid and convenient methodology that makes possible the use of targeting vectors containing large regions of homology so as to modify endogenous genes or chromosomal loci in eukaryotic cells.

In accordance with the present invention, Applicants provide novel methods that enable the use of targeting vectors containing large regions of homology so as to modify endogenous genes or chromosomal loci in eukaryotic cells via homologous recombination. Such methods overcome the above-described limitations of current technologies. In addition, the skilled artisan will readily recognize that the methods of the invention are easily adapted for use with any genomic DNA of any eukaryotic organism including, but not limited to, animals such as mouse, rat, other rodent, or human, as well as plants such as soy, corn and wheat.

SUMMARY OF THE INVENTION

In accordance with the present invention, Applicants have developed a novel, rapid, streamlined, and efficient method for creating and screening eukaryotic cells, which contain modified endogenous genes or chromosomal loci. This novel methods combine, for the first time:
1. Bacterial homologous recombination to precisely engineer a desired genetic modification within a large cloned genomic fragment, thereby creating a large targeting vector for use in eukaryotic cells (LTVECs);
2. Direct introduction of these LTVECs into eukaryotic cells to modify the endogenous chromosomal locus of interest in these cells; and
3. An analysis to determine the rare eukaryotic cells in which the targeted allele has been modified as desired, involving an assay for modification of allele (MOA) of the parental allele that does not require sequence information outside of the targeting sequence, such as, for example, quantitative PCR.

A preferred embodiment of the invention is a method for genetically modifying an endogenous gene or chromosomal locus in eukaryotic cells, comprising: a) obtaining a large cloned genomic fragment containing a DNA sequence of interest; b) using bacterial homologous recombination to genetically modify the large cloned genomic fragment of (a) to create a large targeting vector for use in the eukaryotic cells (LTVEC); c) introducing the LTVEC of (b) into the eukaryotic cells to modify the endogenous gene or chromosomal locus in the cells; and d) using a quantitative assay to detect modification of allele (MOA) in the eukaryotic cells of (c) to identify those eukaryotic cells in which the endogenous gene or chromosomal locus has been genetically modified.

Another embodiment of the invention is a method wherein the genetic modification to the endogenous gene or chromosomal locus comprises deletion of a coding sequence, gene segment, or regulatory element; alteration of a coding sequence, gene segment, or regulatory element; insertion of a new coding sequence, gene segment, or regulatory element; creation of a conditional allele; or replacement of a coding sequence or gene segment from one species with an homologous or orthologous coding sequence from a different species.

An alternative embodiment of the invention is a method wherein the alteration of a coding sequence, gene segment, or regulatory element comprises a substitution, addition, or fusion, wherein the fusion comprises an epitope tag or bifunctional protein.

Yet another embodiment of the invention is a method wherein the quantitative assay comprises quantitative PCR, comparative genomic hybridization, isothermal DNA amplification, quantitative hybridization to an immobilized probe, Invader Probes®, or MMP Assays®, and wherein the quantitative PCR comprises TaqMan® Molecular Beacon, or Eclipse™ probe technology.

Another preferred embodiment of the invention is a method wherein the eukaryotic cell is a mammalian embryonic stem cell and in particular wherein the embryonic stem cell is a mouse, rat, or other rodent embryonic stem cell.

Another preferred embodiment of the invention is a method wherein the endogenous gene or chromosomal locus is a mammalian gene or chromosomal locus, preferably a human gene or chromosomal locus or a mouse, rat, or other rodent gene or chromosomal locus.

An additional preferred embodiment is one in which the LTVEC is capable of accommodating large DNA fragments greater than 20 kb, and in particular large DNA fragments greater than 100 kb.

Another preferred embodiment is a genetically modified endogenous gene or chromosomal locus that is produced by the method of the invention.

Yet another preferred embodiment is a genetically modified eukaryotic cell that is produced by the method of the invention.

A preferred embodiment of the invention is a non-human organism containing the genetically modified endogenous gene or chromosomal locus produced by the method of the invention.

Also preferred in a non-human organism produced from the genetically modified eukaryotic cells or embryonic stem cells produced by the method of the invention.

A preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector (LTVEC) for use in embryonic stem cells; c) introducing the LTVEC of (b) into the embryonic stem cells to modify the endogenous gene or chromosomal locus in the cells; d) using a quantitative assay to detect modification of allele (MOA) in the embryonic stem cells of (c) to identify those embryonic stem cells in which the endogenous gene or chromosomal locus has been genetically modified; e) introducing the embryonic stem cell of (d) into a blastocyst; and f) introducing the blastocyst of (e) into a surrogate mother for gestation.

An additional preferred embodiment of the invention is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c)

to identify those eukaryotic cells in which the endogenous gene or chromosomal locus has been genetically modified; e) removing the nucleus from the eukaryotic cell of (d); f) introducing the nucleus of (e) into an oocyte; and g) introducing the oocyte of (f) into a surrogate mother for gestation.

Yet another preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) fusing the eukaryotic cell of (d) with another eukaryotic cell; f) introducing the fused eukaryotic cell of (e) into a surrogate mother for gestation.

In preferred embodiments, the non-human organism is a mouse, rat, or other rodent; the blastocyst is a mouse, rat, or other rodent blastocyst; the oocyte is a mouse, rat, or other rodent oocyte; and the surrogate mother is a mouse, rat, or other rodent.

Another preferred embodiment is one in which the embryonic stem cell is a mammalian embryonic stem cell, preferably a mouse, rat, or other rodent embryonic stem cell.

An additional preferred embodiment is the use of the genetically modified eukaryotic cells of the invention for the production of a non-human organism, and in particular, the use of the genetically modified embryonic stem cell of the invention for the production of a non-human organism.

A preferred embodiment of the invention is a method for genetically modifying an endogenous gene or chromosomal locus of interest in mouse embryonic stem cells, comprising: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR. Also preferred is a genetically modified mouse embryonic stem cell produced by this method; a mouse containing a genetically modified endogenous gene or chromosomal locus produced by this method; and a mouse produced from the genetically modified mouse embryonic stem cell.

Another preferred embodiment is a mouse containing a genetically modified endogenous gene or chromosomal locus of interest, produced by a method comprising the steps of: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR; e) introducing the mouse embryonic stem cell of (d) into a blastocyst; and f) introducing the blastocyst of (e) into a surrogate mother for gestation.

Also preferred is the use of the genetically modified mouse embryonic stem cell described above for the production of a mouse.

Also preferred are methods wherein 1-5 µg of large targeting vector DNA is introduced into $1 \times 10^7$ eukaryotic cells.

(hb1=homology box 1; hb2=homology box 2; RE=restriction enzyme site).

Figure 2:
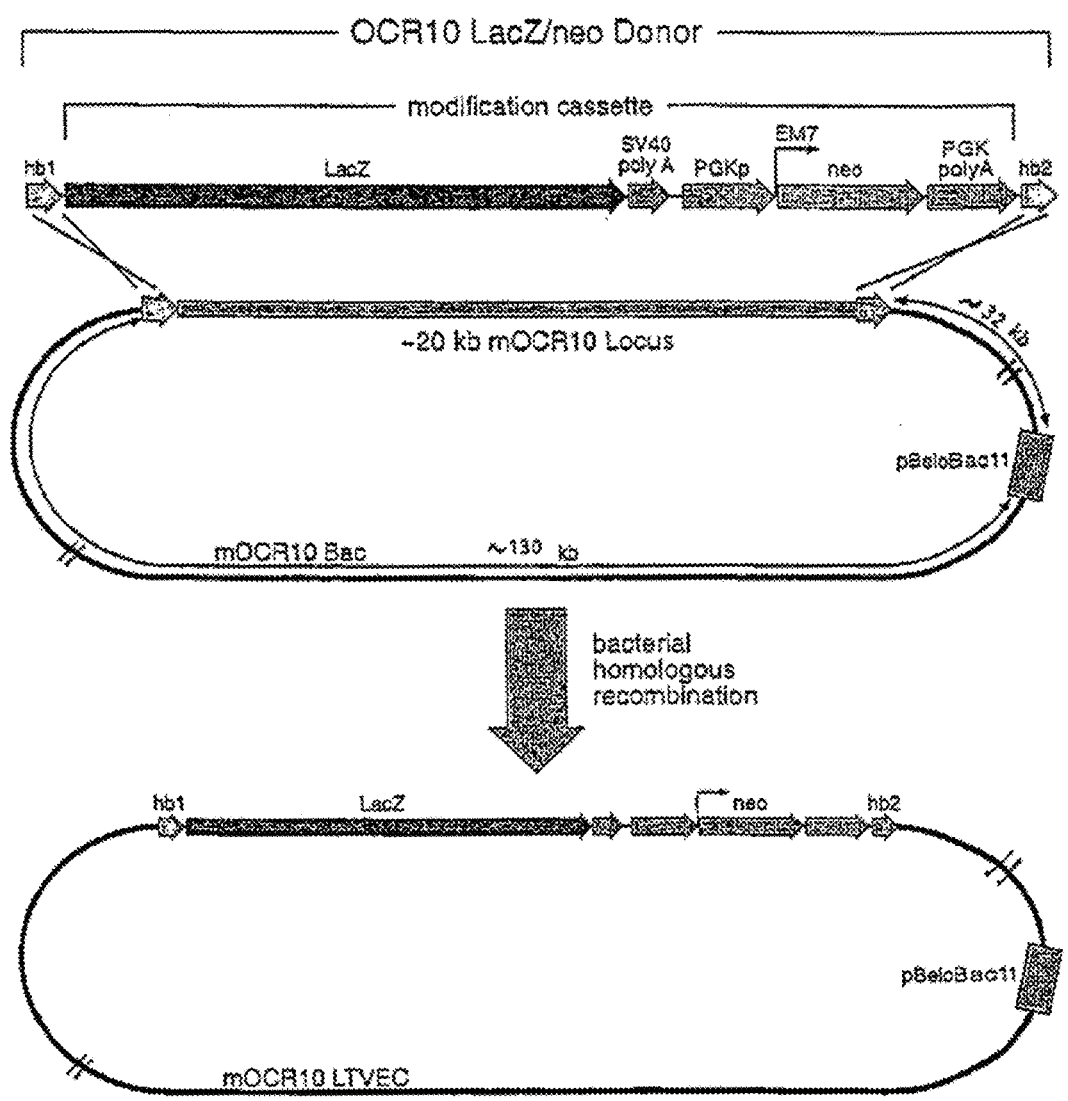

FIG. 2: Schematic diagram of donor fragment and LTVEC for mouse OCR10.

(hb1=homology box 1; lacZ=β-galactosidase ORF; SV40 polyA=a DNA fragment derived from Simian Virus 40, containing a polyadenylation site and signal; PGKp=mouse phosphoglycerate kinase (PGK) promoter; EM7=a bacterial promoter; neo=neomycin phosphotransferase; PGK polyA=3' untranslated region derived from the PGK gene and containing a polyadenylation site and signal; hb2=homology box 2)

FIG. 3A-3D: Sequence of the mouse OCR10 cDNA (SEQ ID NO: 5) and protein (SEQ ID NO: 6), including the positions of homology box 1 (hb1), homology box 2 (hb2), and TaqMan® probes and primers used in a quantitative PCR assay to detect modification of allele (MOA) in ES cells targeted using the mOCR10 LTVEC.

hb1: base pairs 1 to 211
hb2: base pairs 1586 to 1801
TaqMan® probe and corresponding PCR primer set derived from mOCR10 exon 3:
TaqMan® probe: nucleotides 413 to 439—upper strand
Primer ex3-5': nucleotides 390 to 410—upper strand
Primer ex3-3': nucleotides 445 to 461—lower strand
TaqMan® probe and corresponding PCR primer set derived from mOCR10 exon 4:
TaqMan® probe: nucleotides 608 to 639—upper strand
Primer ex4-5': nucleotides 586 to 605—upper strand
Primer ex4-3': nucleotides 642 to 662—lower strand

DEFINITIONS

A "targeting vector" is a DNA construct that contains sequences "homologous" to endogenous chromosomal nucleic acid sequences flanking a desired genetic modification(s). The flanking homology sequences, referred to as "homology arms", direct the targeting vector to a specific chromosomal location within the genome by virtue of the homology that exists between the homology arms and the corresponding endogenous sequence and introduce the desired genetic modification by a process referred to as "homologous recombination".

"Homologous" means two or more nucleic acid sequences that are either identical or similar enough that they are able to hybridize to each other or undergo intermolecular exchange.

"Gene targeting" is the modification of an endogenous chromosomal locus by the insertion into, deletion of, or replacement of the endogenous sequence via homologous recombination using a targeting vector.

A "gene knockout" is a genetic modification resulting from the disruption of the genetic information encoded in a chromosomal locus.

A "gene knockin" is a genetic modification resulting from the replacement of the genetic information encoded in a chromosomal locus with a different DNA sequence.

A "knockout organism" is an organism in which a significant proportion of the organism's cells harbor a gene knockout.

A "knockin organism" is an organism in which a significant proportion of the organism's cells harbor a gene knockin.

A "marker" or a "selectable marker" is a selection marker that allows for the isolation of rare transfected cells expressing the marker from the majority of treated cells in the population. Such marker's gene's include, but are not limited to, neomycin phosphotransferase and hygromycin B phosphotransferase, or fluorescing proteins such as GFP.

An "ES cell" is an embryonic stem cell. This cell is usually derived from the inner cell mass of a blastocyst-stage embryo.

An "ES cell clone" is a subpopulation of cells derived from a single cell of the ES cell population following introduction of DNA and subsequent selection.

A "flanking DNA" is a segment of DNA that is collinear with and adjacent to a particular point of reference.

"LTVECs" are large targeting vectors for eukaryotic cells that are derived from fragments of cloned genomic DNA larger than those typically used by other approaches intended to perform homologous targeting in eukaryotic cells.

A "non-human organism" is an organism that is not normally accepted by the public as being human.

"Modification of allele" (MOA) refers to the modification of the exact DNA sequence of one allele of a gene(s) or chromosomal locus (loci) in a genome. This modification of allele (MOA) includes, but is not limited to, deletions, substitutions, or insertions of as little as a single nucleotide or deletions of many kilobases spanning a gene(s) or chromosomal locus (loci) of interest, as well as any and all possible modifications between these two extremes.

"Orthologous" sequence refers to a sequence from one species that is the functional equivalent of that sequence in another species.

The description and examples presented infra are provided to illustrate the subject invention. One of skill in the art will recognize that these examples are provided by way of illustration only and are not included for the purpose of limiting the invention.

DETAILED DESCRIPTION OF THE INVENTION

Applicants have developed a novel, rapid, streamlined, and efficient method for creating and screening eukaryotic cells, which contain modified endogenous genes or chromosomal loci. In these cells, the modification may be gene(s) knockouts, knockins, point mutations, or large genomic insertions or deletions or other modifications. By way of non-limiting example, these cells may be embryonic stem cells, which are useful for creating knockout or knockin organisms, and in particular, knockout or knockin mice, for the purpose of determining the function of the gene(s) that have been altered, deleted and/or inserted.

The novel methods described herein combine, for the first time:
1. Bacterial homologous recombination to precisely engineer a desired genetic modification within a large cloned genomic DNA fragment, thereby creating a large targeting vector for use in eukaryotic cells (LTVECs);
2. Direct introduction of these LTVECs into eukaryotic cells to modify the corresponding endogenous gene(s) or chromosomal locus (loci) of interest in these cells; and
3. An analysis to determine the rare eukaryotic cells in which the targeted allele has been modified as desired, involving a quantitative assay for modification of allele (MOA) of the parental allele.

It should be emphasized that previous methods to detect successful homologous recombination in eukaryotic cells cannot be utilized in conjunction with the LTVECs of Applicants' invention because of the long homology arms present in the LTVECs. Utilizing a LTVEC to deliberately modify endogenous genes or chromosomal loci in eukaryotic cells via homologous recombination is made possible by the novel application of an assay to determine the rare eukaryotic cells in which the targeted allele has been modified as desired, such assay involving a quantitative assay for modification of allele (MOA) of a parental allele, by employing, for example, quantitative PCR or other suitable quantitative assays for MOA.

The ability to utilize targeting vectors with homology arms larger than those used in current methods is extremely valuable for the following reasons:
1. Targeting vectors are more rapidly and conveniently generated from available libraries containing large genomic inserts (e.g. BAC or PAC libraries) than targeting vectors made using previous technologies, in which the genomic inserts have to be extensively characterized and "trimmed" prior to use (explained in detail below). In addition, minimal sequence information needs to be known about the locus of interest, i.e. it is only necessary to know the approximately 80-100 nucleotides that are required to generate the homology boxes (described in detail below) and to generate probes that can be used in quantitative assays for MOA (described in detail below).
2. Larger modifications as well as modifications spanning larger genomic regions are more conveniently generated and in fewer steps than using previous technologies. For example, the method of the invention makes possible the precise modification of large loci that cannot be accommodated by traditional plasmid-based targeting vectors because of their size limitations. It also makes possible the modification of any given locus at multiple points (e.g. the introduction of specific mutations at different exons of a multi-exon gene) in one step, alleviating the need to engineer multiple targeting vectors and to perform multiple rounds of targeting and screening for homologous recombination in ES cells.

3. The use of long regions of homology (long homology arms) increase the targeting frequency of "hard to target" loci in eukaryotic cells, consistent with previous findings that targeting of homologous recombination in eukaryotic cells appears to be related to the total homology contained within the targeting vector.
4. The increased targeting frequency obtained using long homology arms apparently diminishes the benefit, if any, from using isogenic DNA in these targeting vectors.
5. The application of quantitative MOA assays for screening eukaryotic cells for homologous recombination not only empowers the use of LTVECs as targeting vectors (advantages outlined above) but also reduces the time for identifying correctly modified eukaryotic cells from the typical several days to a few hours. In addition, the application of quantitative MOA does not require the use of probes located outside the endogenous gene(s) or chromosomal locus (loci) that is being modified, thus obviating the need to know the sequence flanking the modified gene(s) or locus (loci). This is a significant improvement in the way the screening has been performed in the past and makes it a much less labor-intensive and much more cost-effective approach to screening for homologous recombination events in eukaryotic cells.

Methods

Many of the techniques used to construct DNA vectors described herein are standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). All DNA sequencing is done by standard techniques using an ABI 373A DNA sequencer and Taq Dideoxy Terminator Cycle Sequencing Kit (Applied Biosystems, Inc., Foster City, Calif.).

Step 1. Obtain a Large Genomic DNA Clone Containing the Gene(s) or Chromosomal Locus (Loci) of Interest.

A Gene(s) or locus (loci) of interest can be selected based on specific criteria, such as detailed structural or functional data, or it can be selected in the absence of such detailed information as potential genes or gene fragments become predicted through the efforts of the various genome-sequencing projects. Importantly, it should be noted that it is not necessary to know the complete sequence and gene structure of a gene(s) of interest to apply the method of the subject invention to produce LTVECs. In fact, the only sequence information that is required is approximately 80-100 nucleotides so as to obtain the genomic clone of interest as well as to generate the homology boxes used in making the LTVEC (described in detail below) and to make probes for use in quantitative MOA assays.

Once a gene(s) or locus (loci) of interest has been selected, a large genomic clone(s) containing this gene(s) or locus (loci) is obtained. This clone(s) can be obtained in any one of several ways including, but not limited to, screening suitable DNA libraries (e.g. BAC, PAC, YAC, or cosmid) by standard hybridization or PCR techniques, or by any other methods familiar to the skilled artisan.

Step 2. Append Homology Boxes 1 and 2 to a Modification Cassette and Generation of LTVEC.

Figure 1:
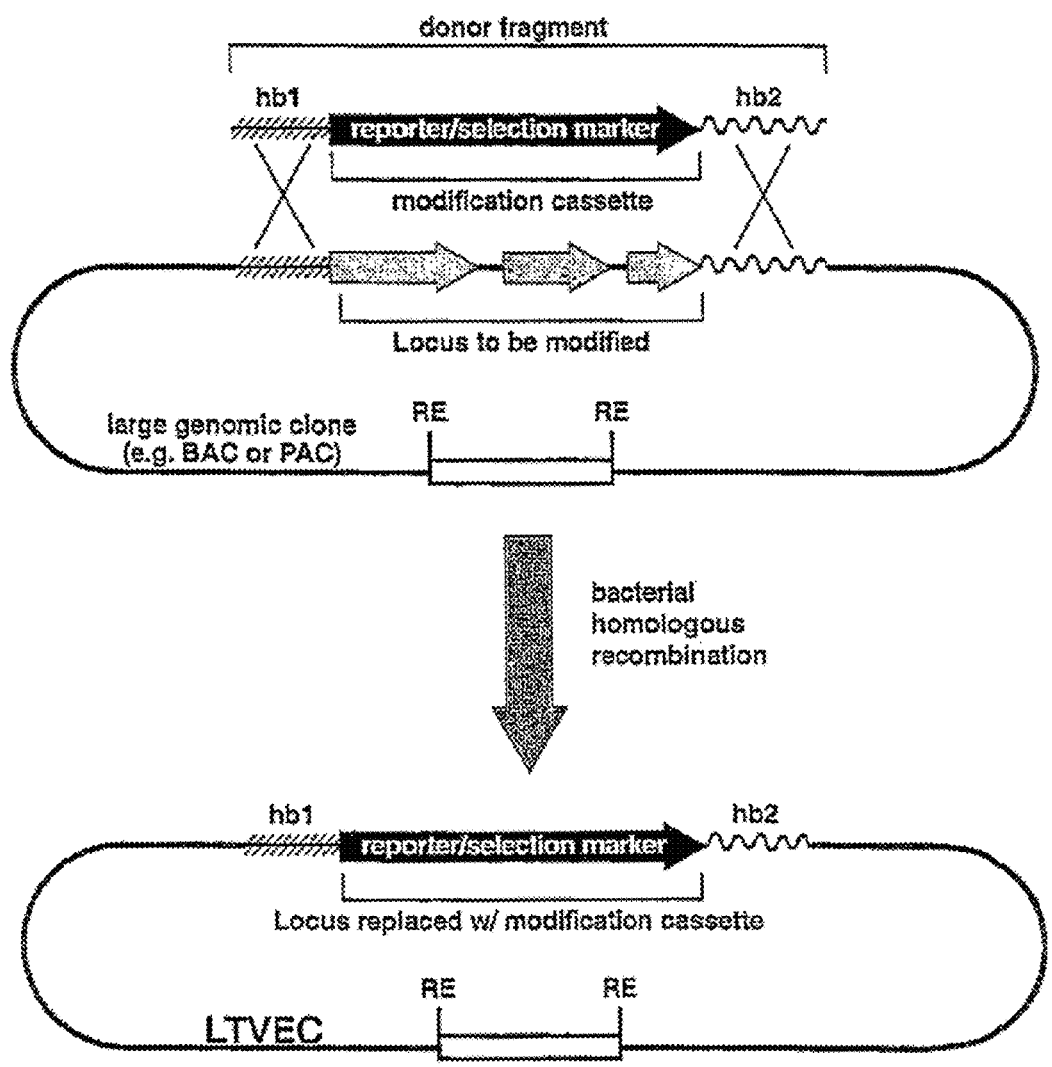
FIG. 1: Schematic diagram of the generation of a typical LTVEC using bacterial homologous recombination.

Homology boxes mark the sites of bacterial homologous recombination that are used to generate LTVECs from large cloned genomic fragments (FIG. 1). Homology boxes are short segments of DNA, generally double-stranded and at least 40 nucleotides in length, that are homologous to regions within the large cloned genomic fragment flanking the "region to be modified". The homology boxes are appended to the modification cassette, so that following homologous recombination in bacteria, the modification cassette replaces the region to be modified (FIG. 1). The technique of creating a targeting vector using bacterial homologous recombination can be performed in a variety of systems (Yang et al., Nat Biotechnol, 15:859-65, 1997; Muyrers et al., Nucleic Acids Res, 27:1555-7, 1999; Angrand et al., Nucleic Acids Res, 27:e16, 1999; Narayanan et al., Gene Ther, 6:442-7, 1999; Yu, et al., Proc Natl Acad Sci USA, 97:5978-83, 2000). One example of a favored technology currently in use is ET cloning (Zhang et al., Nat Genet, 20:123-8, 1998; Narayanan et al., Gene Ther, 6:442-7, 1999) and variations of this technology (Yu, et al., Proc Natl Acad Sci USA, 97:5978-83, 2000). ET refers to the recE (Hall and Kolodner, Proc Natl Acad Sci USA, 91:3205-9, 1994) and recT proteins (Kusano et al., Gene, 138:17-25, 1994) that carry out the homologous recombination reaction. RecE is an exonuclease that trims one strand of linear double-stranded DNA (essentially the donor DNA fragment described infra) 5' to 3', thus leaving behind a linear double-stranded fragment with a 3' single-stranded overhang. This single-stranded overhang is coated by recT protein, which has single-stranded DNA (ssDNA) binding activity (Kovall and Matthews, Science, 277:1824-7, 1997). ET cloning is performed using $E.\ coli$ that transiently express the $E.\ coli$ gene products of recE and recT (Hall and Kolodner, Proc Natl Acad Sci USA, 91:3205-9, 1994; Clark et al., Cold Spring Harb Symp Quant Biol, 49:453-62, 1984; Noirot and Kolodner, J Biol Chem, 273:12274-80, 1998; Thresher et al., J Mol Biol, 254:364-71, 1995; Kolodner et al., Mol Microbiol, 11:23-30, 1994; Hall et al., J Bacteriol, 175:277-87, 1993) and the bacteriophage lambda (λ) protein λgam (Murphy, J Bacteriol, 173:5808-21, 1991; Poteete et al., J Bacteriol, 170:2012-21, 1988). The λgam protein is required for protecting the donor DNA fragment from degradation by the recBC exonuclease system (Myers and Stahl, Annu Rev Genet, 28:49-70, 1994) and it is required for efficient ET-cloning in recBC$^+$ hosts such as the frequently used $E.\ coli$ strain DH10b.

The region to be modified and replaced using bacterial homologous recombination can range from zero nucleotides in length (creating an insertion into the original locus) to many tens of kilobases (creating a deletion and/or a replacement of the original locus). Depending on the modification cassette, the modification can result in the following:

(a) deletion of coding sequences, gene segments, or regulatory elements;

(b) alteration(s) of coding sequence, gene segments, or regulatory elements including substitutions, additions, and fusions (e.g. epitope tags or creation of bifunctional proteins such as those with GFP);

(c) insertion of new coding regions, gene segments, or regulatory elements, such as those for selectable marker genes or reporter genes or putting new genes under endogenous transcriptional control;

(d) creation of conditional alleles, e.g. by introduction of loxP sites flanking the region to be excised by Cre recombinase (Abremski and Hoess, J Biol Chem, 259:1509-14, 1984), or FRT sites flanking the region to be excised by Flp recombinase (Andrews et al., Cell, 40:795-803, 1985; Meyer-Leon et al., Cold Spring Harb Symp Quant Biol, 49:797-804, 1984; Cox, Proc Natl Acad Sci USA, 80:4223-7, 1983); or (e) replacement of coding sequences or gene segments from one species with orthologous coding sequences from a different species, e.g. replacing a murine genetic locus with the orthologous human genetic locus to engineer a mouse where that particular locus has been 'humanized'.

Any or all of these modifications can be incorporated into a LTVEC. A specific, non-limiting example in which an endogenous coding sequence is entirely deleted and simultaneously replaced with both a reporter gene as well as a selectable marker is provided below in Example 1, as are the advantages of the method of the invention as compared to previous technologies.

Step 3 (Optional). Verify that Each LTVEC has been Engineered Correctly.

Verify that each LTVEC has been engineered correctly by:
a. Diagnostic PCR to verify the novel junctions created by the introduction of the donor fragment into the gene(s) or chromosomal locus (loci) of interest. The PCR fragments thus obtained can be sequenced to further verify the novel junctions created by the introduction of the donor fragment into the gene(s) or chromosomal locus (loci) of interest.
b. Diagnostic restriction enzyme digestion to make sure that only the desired modifications have been introduced into the LTVEC during the bacterial homologous recombination process.
c. Direct sequencing of the LTVEC, particularly the regions spanning the site of the modification to verify the novel junctions created by the introduction of the donor fragment into the gene(s) or chromosomal locus (loci) of interest.

Step 4. Purification, Preparation, and Linearization of LTVEC DNA for Introduction into Eukaryotic Cells.
a. Preparation of LTVEC DNA:

Prepare miniprep DNA (Sambrook, J., E. F. Fritsch And T. Maniatis. Molecular Cloning: A Laboratory Manual, Second Edition, Vols 1, 2, and 3, 1989; Tillett and Neilan, Biotechniques, 24:568-70, 572, 1998; http://www.giagen.com/literature/handbooks/plkmini/plm_399.pdf) of the selected LTVEC and re-transform the miniprep LTVEC DNA into E. coli using electroporation (Sambrook, J., E. F. Fritsch and T. Maniatis, Molecular Cloning: A Laboratory Manual, Second Edition, Vols 1, 2, and 3, 1989). This step is necessary to get rid of the plasmid encoding the recombinogenic proteins that are utilized for the bacterial homologous recombination step (Zhang et al., Nat Genet, 20:123-8, 1998; Narayanan et al., Gene Ther, 6:442-7, 1999). It is useful to get rid of this plasmid (a) because it is a high copy number plasmid and may reduce the yields obtained in the large scale LTVEC preps; (b) to eliminate the possibility of inducing expression of the recombinogenic proteins; and (c) because it may obscure physical mapping of the LTVEC. Before introducing the LTVEC into eukaryotic cells, larger amounts of LTVEC DNA are prepared by standard methodology (http://www.qiagen.comiliterature/handbooks/plk/plklow.pdf; Sambrook, J., E. F. Fritsch And T. Maniatis. Molecular Cloning: A Laboratory Manual, Second Edition, Vols 1, 2, and 3, 1989; Tillett and Neilan, Biotechniques, 24:568-70, 572, 1998). However, this step can be bypassed if a bacterial homologous recombination method that utilizes a recombinogenic prophage is used, i.e. where the genes encoding the recombinogenic proteins are integrated into the bacterial chromosome (Yu, et al., Proc Natl Acad Sci USA, 97:5978-83, 2000), is used.
b. Linearizing the LTVEC DNA:

To prepare the LTVEC for introduction into eukaryotic cells, the LTVEC is preferably linearized in a manner that leaves the modified endogenous gene(s) or chromosomal locus (loci) DNA flanked with long homology arms. This can be accomplished by linearizing the LTVEC, preferably in the vector backbone, with any suitable restriction enzyme that digests only rarely. Examples of suitable restriction enzymes include NotI, PacI, SfiI, SrfI, SwaI, FseI, etc. The choice of restriction enzyme may be determined experimentally (i.e. by testing several different candidate rare cutters) or, if the sequence of the LTVEC is known, by analyzing the sequence and choosing a suitable restriction enzyme based on the analysis. In situations where the LTVEC has a vector backbone containing rare sites such as CosN sites, then it can be cleaved with enzymes recognizing such sites, for example λ terminase (Shizuya et al., Proc Natl Acad Sci USA, 89:8794-7, 1992; Becker and Gold, Proc Natl Acad Sci USA, 75:4199-203, 1978; Rackwitz et al., Gene, 40:259-66, 1985).

Step 5. Introduction of LTVEC into Eukaryotic Cells and Selection of Cells where Successful Introduction of the LTVEC has Taken Place.

LTVEC DNA can be introduced into eukaryotic cells using standard methodology, such as transfection mediated by calcium phosphate, lipids, or electroporation (Sambrook, J., E. F. Fritsch And T. Maniatis. Molecular Cloning: A Laboratory Manual, Second Edition, Vols 1, 2, and 3, 1989). The cells where the LTVEC has been introduced successfully can be selected by exposure to selection agents, depending on the selectable marker gene that has been engineered into the LTVEC. As a non-limiting example, if the selectable marker is the neomycin phosphotransferase (neo) gene (Beck, et al., Gene, 19:327-36, 1982), then cells that have taken up the LTVEC can be selected in G418-containing media; cells that do not have the LTVEC will die whereas cells that have taken up the LTVEC will survive (Santerre, et al., Gene, 30:147-56, 1984). Other suitable selectable markers include any drug that has activity in eukaryotic cells (Joyner, The Practical Approach Series, 293, 1999), such as hygromycin B (Santerre, et al., Gene, 30:147-56, 1984; Bernard, et al., Exp Cell Res, 158:237-43, 1985; Giordano and McAllister, Gene, 88:285-8, 1990), Blasticidin S (Izumi, et al., Exp Cell Res, 197:229-33, 1991), and other which are familiar to those skilled in the art.

Step 6. Screen for Homologous Recombination Events in Eukaryotic Cells Using Quantitative Assay for Modification of Allele (MOA).

Eukaryotic cells that have been successfully modified by targeting the LTVEC into the locus of interest can be identified using a variety of approaches that can detect modification of allele within the locus of interest and that do not depend on assays spanning the entire homology arm or arms.

Such approaches can include but are not limited to:
(a) quantitative PCR using TaqMan® (Lie and Petropoulos, Curr Opin Biotechnol, 9:43-8, 1998);
(b) quantitative MOA assay using molecular beacons (Tan, et al., Chemistry, 6:1107-11, 2000)
(c) fluorescence in situ hybridization FISH (Laan, et al., Hum Genet, 96:275-80, 1995) or comparative genomic hybridization (CGH) (Forozan, et al., Trends Genet, 13:405-9, 1997; Thompson and Gray, J Cell Biochem Suppl, 139-43, 1993; Houldsworth and Chaganti, Am J Pathol, 145: 1253-60, 1994);
(d) isothermic DNA amplification (Lizardi, et al., Nat Genet, 19:225-32, 1998; Mitra and Church, Nucleic Acids Res, 27:e34, 1999);
(e) quantitative hybridization to an immobilized probe(s) (Southern, J. Mol. Biol. 98: 503, 1975; Kafatos F C; Jones C W; Efstratiadis A, Nucleic Acids Res 7(6):1541-52, 1979);
(f) Invader Probes® (Third Wave Technologies);

(g) Eclipse™ and Molecular Beacon probes (Synthetic Genetics); and (h) MMP assays (High Throughput Genomics)

Applicants provide herein an example in which TaqMan® quantitative PCR is used to screen for successfully targeted eukaryotic cells. In this non-limiting example, TaqMan® is used to identify eukaryotic cells, which have undergone homologous recombination wherein a portion of one of two endogenous alleles in a diploid genome has been replaced by another sequence. In contrast to traditional methods, in which a difference in restriction fragment length spanning the entire homology arm or arms indicates the modification of one of two alleles, the quantitative TaqMan® method will detect the modification of one allele by measuring the reduction in copy number (by half) of the unmodified allele. Specifically, the probe detects the unmodified allele and not the modified allele. Therefore, the method is independent of the exact nature of the modification and not limited to the sequence replacement described in this example. TaqMan is used to quantify the number of copies of a DNA template in a genomic DNA sample, especially by comparison to a reference gene (Lie and Petropoulos, Curr Opin Biotechnol, 9:43-8, 1998). The reference gene is quantitated in the same genomic DNA as the target gene(s) or locus (loci). Therefore, two TaqMan® amplifications (each with its respective probe) are performed. One TaqMan® probe determines the "Ct" (Threshold Cycle) of the reference gene, while the other probe determines the Ct of the region of the targeted gene(s) or locus (loci) which is replaced by successful targeting. The Ct is a quantity that reflects the amount of starting DNA for each of the TaqMan® probes, i.e. a less abundant sequence requires more cycles of PCR to reach the threshold cycle. Decreasing by half the number of copies of the template sequence for a TaqMan® reaction will result in an increase of about one Ct unit. TaqMan® reactions in cells where one allele of the target gene(s) or locus (loci) has been replaced by homologous recombination will result in an increase of one Ct for the target TaqMan® reaction without an increase in the Ct for the reference gene when compared to DNA from non-targeted cells. This allows for ready detection of the modification of one allele of the gene(s) of interest in eukaryotic cells using LTVECs.

As stated above, modification of allele (MOA) screening is the use of any method that detects the modification of one allele to identify cells, which have undergone homologous recombination. It is not a requirement that the targeted alleles be identical (homologous) to each other, and in fact, they may contain polymorphisms, as is the case in progeny resulting from crossing two different strains of mice. In addition, one special situation that is also covered by MOA screening is targeting of genes which are normally present as a single copy in cells, such as some of the located on the sex chromosomes and in particular, on the Y chromosome. In this case, methods that will detect the modification of the single targeted allele, such as quantitative PCR, Southern blottings, etc., can be used to detect the targeting event. It is clear that the method of the invention can be used to generate modified eukaryotic cells even when alleles are polymorphic or when they are present in a single copy in the targeted cells.

Step 8. Uses of Genetically Modified Eukaryotic Cells.

(a) The genetically modified eukaryotic cells generated by the methods described in steps 1 through 7 can be employed in any in vitro or in vivo assay, where changing the phenotype of the cell is desirable.

(b) The genetically modified eukaryotic cell generated by the methods described in steps 1 through 7 can also be used to generate an organism carrying the genetic modification. The genetically modified organisms can be generated by several different techniques including but not limited to:

1. Modified embryonic stem (ES) cells such as the frequently used rat and mouse ES cells. ES cells can be used to create genetically modified rats or mice by standard blastocyst injection technology or aggregation techniques (Robertson, Practical Approach Series, 254, 1987; Wood, et al., Nature, 365:87-9, 1993; Joyner, The Practical Approach Series, 293, 1999), tetraploid blastocyst injection (Wang, et al., Mech Dev, 62:137-45, 1997), or nuclear transfer and cloning (Wakayama, et al., Proc Natl Acad Sci USA, 96:14984-9, 1999). ES cells derived from other organisms such as rabbits (Wang, et al., Mech Dev, 62:137-45, 1997; Schoonjans, et al., Mol Reprod Dev, 45:439-43, 1996) or chickens (Pain, et al., Development, 122:2339-48, 1996) or other species should also be amenable to genetic modification(s) using the methods of the invention.

2. Modified protoplasts can be used to generate genetically modified plants (for example see U.S. Pat. No. 5,350,689 "Zea mays plants and transgenic Zea mays plants regenerated from protoplasts or protoplast-derived cells", and U.S. Pat. No. 5,508,189 "Regeneration of plants from cultured guard cell protoplasts" and references therein).

3. Nuclear transfer from modified eukaryotic cells to oocytes to generate cloned organisms with modified allele (Wakayama, et al., Proc Natl Acad Sci USA, 96:14984-9, 1999; Baguisi, et al., Nat Biotechnol, 17:456-61, 1999; Wilmut, et al., Reprod Fertil Dev, 10:639-43, 1998; Wilmut, et al., Nature, 385:810-3, 1997; Wakayama, et al., Nat Genet, 24:108-9, 2000; Wakayama, et al., Nature, 394:369-74, 1998; Rideout, et al., Nat Genet, 24:109-10, 2000; Campbell, et al., Nature, 380:64-6, 1996).

4. Cell-fusion to transfer the modified allele to another cell, including transfer of engineered chromosome(s), and uses of such cell(s) to generate organisms carrying the modified allele or engineered chromosome(s) (Kuroiwa, et al., Nat Biotechnol, 18:1086-1090, 2000).

5. The method of the invention are also amenable to any other approaches that have been used or yet to be discovered.

While many of the techniques used in practicing the individual steps of the methods of the invention are familiar to the skilled artisan, Applicants contend that the novelty of the method of the invention lies in the unique combination of those steps and techniques coupled with the never-before-described method of introducing a LTVEC directly into eukaryotic cells to modify a chromosomal locus, and the use of quantitative MOA assays to identify eukaryotic cells which have been appropriately modified. This novel combination represents a significant improvement over previous technologies for creating organisms possessing modifications of endogenous genes or chromosomal loci.

EXAMPLES

Example 1: Engineering Mouse ES Cells Bearing a Deletion of the OCR10 Gene a. Selection of a Large Genomic DNA Clone Containing mOCR10

A Bacterial Artificial Chromosome (BAC) clone carrying a large genomic DNA fragment that contained the coding sequence of the mouse OCR10 (mOCR10) gene was obtained by screening an arrayed mouse genomic DNA BAC library (Incyte Genomics) using PCR. The primers employed to screen this library were derived from the mOCR10 gene cDNA sequence.

Two primer pairs where used:

```
(a) OCR10.RAA
                                    SEQ ID NO: 1
    (5'-AGCTACCAGCTGCAGATGCGGGCAG-3');
    and OCR10.PVIrc
                                    SEQ ID NO: 2
    (5'-CTCCCCAGCCTGGGTCTGAAAGATGACG-3');
    which amplifies a 102 bp DNA;
    and (b) OCR10.TDY
                                    SEQ ID NO: 3
    (5'-GACCTCACTTGCTACACTGACTAC-3');
    and OCR10.QETrc
                                    SEQ ID NO: 4
    (5'-ACTTGTGTAGGCTGCAGAAGGTCTCTTG-3');
    which amplifies a 1500 bp DNA.
```

This mOCR10 BAC contained approximately 180 kb of genomic DNA including the complete mOCR10 coding sequence. This BAC clone was used to generate an LTVEC which was subsequently used to delete a portion of the coding region of mOCR10 while simultaneously introducing a reporter gene whose initiation codon precisely replaced the initiation codon of OCR10, as well as insertion of a selectable marker gene useful for selection both in *E. coli* and mammalian cells following the reporter gene (FIG. 2). The reporter gene (in this non-limiting example LacZ, the sequence of which is readily available to the skilled artisan), encodes the *E. coli* β-galactosidase enzyme. Because of the position of insertion of LacZ (its initiating codon is at the same position as the initiation codon of mOCR10) the expression of lacZ should mimic that of mOCR10, as has been observed in other examples where similar replacements with LacZ were performed using previous technologies (see "Gene trap strategies in ES cells", by W Wurst and A. Gossler, in Joyner, The Practical Approach Series, 293, 1999). The LacZ gene allows for a simple and standard enzymatic assay to be performed that can reveal its expression patterns in situ, thus providing a surrogate assay that reflects the normal expression patterns of the replaced gene(s) or chromosomal locus (loci).

b. Construction of Donor Fragment and Generation of LTVEC

The modification cassette used in the construction of the mOCR10 LTVEC is the lacZ-SV40 polyA-PGKp-EM7-neo-PGK polyA cassette wherein lacZ is a marker gene as described above, SV40 polyA is a fragment derived from Simian Virus 40 (Subramanian, et al., Prog Nucleic Acid Res Mol Biol, 19:157-64, 1976; Thimmappaya, et al., J Biol Chem, 253:1613-8, 1978; Dhar, et al., Proc Natl Acad Sci USA, 71:371-5, 1974; Reddy, et al., Science, 200:494-502, 1978) and containing a polyadenylation site and signal (Subramanian, et al., Prog Nucleic Acid Res Mol Biol, 19:157-64, 1976; Thimmappaya, et al., J Biol Chem, 253: 1613-8, 1978; Dhar, et al., Proc Natl Acad Sci USA, 71:371-5, 1974; Reddy, et al., Science, 200:494-502, 1978), PGKp is the mouse phosphoglycerate kinase (PGK) promoter (Adra, et al., Gene, 60:65-74, 1987) (which has been used extensively to drive expression of drug resistance genes in mammalian cells), EM7 is a strong bacterial promoter that has the advantage of allowing for positive selection in bacteria of the completed LTVEC construct by driving expression of the neomycin phosphotransferase (neo) gene, neo is a selectable marker that confers Kanamycin resistance in prokaryotic cells and G418 resistance in eukaryotic cells (Beck, et al., Gene, 19:327-36, 1982), and PGK polyA is a 3' untranslated region derived from the PGK gene and containing a polyadenylation site and signal (Boer, et al., Biochem Genet, 28:299-308, 1990).

To construct the mOCR10 LTVEC, first a donor fragment was generated consisting of a mOCR10 homology box 1 (hb1) attached upstream from the LacZ gene in the modification cassette and a mOCR10 homology box 2 (hb2) attached downstream of the neo-PGK polyA sequence in the modification cassette (FIG. 2), using standard recombinant genetic engineering technology. Homology box 1 (hb1) consists of 211 bp of untranslated sequence immediately upstream of the initiating methionine of the mOCR10 open reading frame (mOCR10 ORF) (FIG. 3A-3D). Homology box 2 (hb2) consists of last 216 bp of the mOCR10 ORF, ending at the stop codon (FIG. 3A-3D).

Subsequently, using bacterial homologous recombination (Zhang, et al., Nat Genet, 20:123-8, 1998; Angrand, et al., Nucleic Acids Res, 27:e16, 1999; Muyrers, et al., Nucleic Acids Res, 27:1555-7, 1999; Narayanan, et al., Gene Ther, 6:442-7, 1999; Yu, et al., Proc Natl Acad Sci USA, 97:5978-83, 2000), this donor fragment was used to precisely replace the mOCR10 coding region (from initiation methionine to stop codon) with the insertion cassette, resulting in construction of the mOCR10 LTVEC (FIG. 2). Thus, in this mOCR10 LTVEC, the mOCR10 coding sequence was replaced by the insertion cassette creating an approximately 20 kb deletion in the mOCR10 locus while leaving approximately 130 kb of upstream homology (upstream homology arm) and 32 kb of downstream homology (downstream homology arm).

It is important to note that LTVECs can be more rapidly and conveniently generated from available BAC libraries than targeting vectors made using previous technologies because only a single bacterial homologous recombination step is required and the only sequence information required is that needed to generate the homology boxes. In contrast, previous approaches for generating targeting vectors using bacterial homologous recombination require that large targeting vectors be "trimmed" prior to their introduction in ES cells (Hill et al., Genomics, 64:111-3, 2000). This trimming is necessary because of the need to generate homology arms short enough to accommodate the screening methods utilized by previous approaches. One major disadvantage of the method of Hill et al. is that two additional homologous recombination steps are required simply for trimming (one to trim the region upstream of the modified locus and one to trim the region downstream of the modified locus). To do this, substantially more sequence information is needed, including sequence information spanning the sites of trimming.

In addition, another obvious advantage, illustrated by the above example, is that a very large deletion spanning the mOCR10 gene (approximately 20 kb) can be easily generated in a single step. In contrast, using previous technologies, to accomplish the same task may require several steps and may involve marking the regions upstream and downstream of the coding sequences with loxP sites in order to use the Cre recombinase to remove the sequence flanked by these sites after introduction of the modified locus in eukaryotic cells. This may be unattainable in one step, and thus may require the construction of two targeting vectors using different selection markers and two sequential targeting events in ES cells, one to introduce the loxP site at the region upstream of the coding sequence and another to introduce the loxP site at the region downstream of the coding sequence. It should be further noted that the creation of large deletions often occurs with low efficiency using the previous targeting technologies in eukaryotic cells, because the frequency of achieving homologous recombination may be low when using targeting vectors containing large deletion flanked by relatively short homology arms. The high efficiency obtained using the method of the invention (see below) is due to the very long homology arms present in the LTVEC that increase the rate of homologous recombination in eukaryotic cells.

c. Verification, Preparation, and Introduction of mOCR10 LTVEC DNA into ES Cells The sequence surrounding the junction of the insertion cassette and the homology sequence was verified by DNA sequencing. The size of the mOCR10 LTVEC was verified by restriction analysis followed by pulsed field gel electrophoresis (PFGE) (Cantor, et al., Annu Rev Biophys Biophys Chem, 17:287-304, 1988; Schwartz and Cantor, *Cell,* 37:67-75, 1984). A standard large-scale plasmid preparation of the mOCR10 LTVEC was done, the plasmid DNA was digested with the restriction enzyme NotI, which cuts in the vector backbone of the mOCR10 LTVEC, to generate linear DNA. Subsequently the linearized DNA was introduced into mouse ES cells by electroporation (Robertson, Practical Approach Series, 254, 1987; Joyner, The Practical Approach Series, 293, 1999; Sambrook, et al., Sambrook, J., E. F. Fritsch and T. Maniatis. Molecular Cloning: A Laboratory Manual, Second Edition, Vols 1, 2, and 3, 1989). ES cells successfully transfected with the mOCR10 LTVEC were selected for in G418-containing media using standard selection methods (Robertson, Practical Approach Series, 254, 1987; Joyner, The Practical Approach Series, 293, 1999).

d. Identification of Targeted ES Cells Clones Using a Quantitative Modification of Allele (MOA) Assay To identify ES cells in which one of the two endogenous mOCR10 genes had been replaced by the modification cassette sequence, DNA from individual ES cell clones was analyzed by quantitative PCR using standard TaqMan® methodology as described (Applied Biosystems, TaqMan® Universal PCR Master Mix, catalog number P/N 4304437; see also http://www.pebiodocs.com/pebiodocs/04304449.pdf). The primers and TaqMan® probes used are as described in FIG. 3A-3D. A total of 69 independent ES cells clones where screened and 3 were identified as positive, i.e. as clones in which one of the endogenous mOCR10 coding sequence had been replaced by the modification cassette described above.

Several advantages of the MOA approach are apparent:
(i) It does not require the use of a probe outside the locus being modified, thus obviating the need to know the sequence flanking the modified locus.
(ii) It requires very little time to perform compared to conventional Southern blot methodology which has been the previous method of choice (Robertson, Practical Approach Series, 254, 1987, Joyner, The Practical Approach Series, 293, 1999), thus reducing the time for identifying correctly modified cells from the typical several days to just a few hours.

This is a significant improvement in the way screening has been performed in the past and makes it a much less labor-intensive and more cost-effective approach to screening for homologous recombination events in eukaryotic cells.

Yet another advantage of the method of the invention is that it is also superior to previous technologies because of its ability to target difficult loci. Using previous technologies, it has been shown that for certain loci the frequency of successful targeting may by as low as 1 in 2000 integration events, perhaps even lower. Using the method of the invention, Applicants have demonstrated that such difficult loci can be targeted much more efficiently using LTVECs that contain long homology arms (i.e. greater than those allowed by previous technologies). As the non-limiting example described above demonstrates, the Applicants have targeted the OCR10 locus, a locus that has previously proven recalcitrant to targeting using conventional technology. Using the method of the invention, Applicants have shown that they have obtained successful targeting in 3 out of 69 ES cells clones in which the mOCR10 LTVEC (containing more than 160 kb of homology arms, and introducing a 20 kb deletion) had integrated, whereas using previous technology for ES cell targeting (Joyner, The Practical Approach Series, 293, 1999) using a plasmid-based vector with homology arms shorter than 10-20 kb while also introducing a deletion of less than 15 kb, no targeted events were identified among more than 600 integrants of the vector. These data clearly demonstrate the superiority of the method of the invention over previous technologies.

Example 2: Increased Targeting Frequency and Abrogation of the Need to Use Isogenic DNA when LTVECs are Used as the Targeting Vectors As noted above, the increased targeting frequency obtained using long homology arms should diminish the benefit, if any, derived from using genomic DNA in constructing LTVECs that is isogenic with (i.e. identical in sequence to) the DNA of the eukaryotic cell being targeted. To test this hypothesis, Applicants have constructed several LTVECs using genomic DNA derived from the same mouse substrain as the eukaryotic cell to be targeted (presumably isogenic), and a large number of other LTVECs using genomic DNA derived from mouse substrains differing from that of the eukaryotic cell to be targeted (presumably non-isogenic). The non-isogenic LTVECs exhibited an average targeting frequency of 6% (ranging from 1-20%, Table 1), while the isogenic LTVECs exhibited as average targeting frequency of 3% (ranging from 2-5%), indicating that the rate of successful targeting using LTVECs does not depend on isogenicity.

TABLE 1

| Target Gene | Description | DNA Origin | ES Cell | BAC Size | Arm 1 | Arm 2 | Deletion | Positive Clones | % Targeting |
|---|---|---|---|---|---|---|---|---|---|
| NON-ISOGENIC | | | | | | | | | |
| OGH | LacZ-ATG fusion | SvJ | CJ7 | 148 | 50 | 90 | 5 | 4 | 4 |
| OCR10(A) | LacZ-ATG fusion | SvJ | CJ7 | 165 | 135 | 8 | 20 | 1 | 1.4 |
| OCR10(B) | LacZ-ATG fusion | SvJ | CJ7 | 160 | 130 | 32 | 20 | 3 | 4.3 |
| MA61 | LacZ-ATG fusion | SvJ | CJ7 | 95 | N/D | N/D | 30 | 3 | 4.6 |
| MA16 | LacZ-ATG fusion | SvJ | CJ7 | 120 | N/D | N/D | 8 | 8 | 13 |
| AGRP | LacZ-ATG fusion | SvJ | CJ7 | 189 | 147 | 32 | 8 | 1 | 1.1 |
| SHIP-2 | LacZ-ATG fusion | SvJ | CJ7 | 136 | 30 | 90 | 11 | 7 | 15 |
| Sm22 | LacZ-ATG fusion | SvJ | CJ7 | 70 | 35 | 35 | 0.9 | 18 | 20 |
| LGR7L | LacZ-ATG fusion | SvJ | CJ7 | 200 | N/D | N/D | 1 | 3 | 3.2 |
| C5aR | LacZ-ATG fusion | SvJ | CJ7 | 160 | 80 | 25 | 1 | 4 | 4.2 |
| IL18 | LacZ-ATG fusion | SvJ | CJ7 | 120 | 50 | 65 | 10 | 7 | 7.3 |
| PLGF | LacZ-ATG fusion | SvJ | CJ7 | 130 | 40 | 20 | 8 | 1 | 1 |
| NaDC-1 | LacZ-ATG fusion | SvJ | CJ7 | 180 | 30 | 45 | 25 | 4 | 2.1 |
| ISOGENIC | | | | | | | | | |
| ROR1 | Intracell-LacZ fusion | CJ7 | CJ7 | 55 | 14 | 14 | 20 | 5 | 5 |
| ROR1 | Intracell-3xmyc fusion | CJ7 | CJ7 | 55 | 14 | 14 | 20 | 2 | 2 |
| ROR2 | Brachydactyly mutation and Myc tag | CJ7 | CJ7 | 45 | 11 | 24 | 0.5 | 2 | 2 |

(Approximate Size (kb) spans BAC Size, Arm 1, Arm 2, Deletion columns)

Example 3: Detailed Description of the TaqMan®-Based MOA for Identification of Targeted ES Clones ES cell clones that have taken up the LTVEC and incorporated it into the genome at the targeted locus by homologous recombination are identified by a modification of allele (MOA) assay that uses real-time quantitative PCR to discern the difference between targeted ES cell clones, in which one of the two targeted alleles is modified, and non-targeted ES cell clones, in which both alleles remain unmodified. The MOA assay consists of a primary and a secondary screen. The primary screen contains the following steps: (1) growth of LTVEC-transfected ES cell clones on gelatin-coated 96-well plates; (2) isolation of genomic DNA from each ES cell clone; (3) use of each genomic DNA sample as a template in 8 separate quantitative PCRs on two 384-well plates in which 2 of the PCRs employ a target-locus-specific primer set that hybridizes to DNA sequences at one end of the genomic fragment targeted for deletion ('upstream PCR'), 2 of the PCRs employ a target-locus-specific primer set that hybridizes to DNA sequences at the other end of the genomic fragment targeted for deletion ('downstream PCR'), 4 of the PCRs employ primer sets that recognize four non-targeted reference loci ('reference PCRs'), and each PCR includes a fluorescent probe (for example a TaqMan® [ABI], Eclipse™, or Molecular Beacon probe [Synthetic Genetics]) that recognizes the amplified sequence and whose fluorescence signal is directly proportional to the amount of PCR product; (4) running the PCRs in a device that combines a thermocycler with a fluorescence detector (for example the ABI 7900HT) that quantifies the accumulation of amplification products during the PCR and determines the threshold cycle ($C_T$), the point in the PCR at which the fluorescence signal is detectable above background noise; (5) for each ES cell clone DNA sample, calculation of the difference in the $C_T$ values ($\Delta C_T$) between the upstream PCRs and each of the four reference PCRs and between the downstream PCRs and each of the four reference PCRs to create 8 tables of 96 $\Delta C_T$ values; (6) normalization of the $\Delta C_T$ values to positive values; (7) calculation of the median $\Delta C_T$ value for each target-reference comparison table; (8) determination of a confidence score by use of a computer program that examines the eight $\Delta C_T$ tables and calculates the number of times a given ES cell clone DNA sample produces a $\Delta C_T$ value within the tolerance ranges 0.5 to 1.5, 0.25 to 1.5, 0.5 to 2.0, 0.25 to 2.0, 0.5 to 3.0 and 0.25 to 3.0 cycles greater than the median $\Delta C_T$ (examples of computer programming languages suitable for creating or writing such a program include visual basics, Java, or any other computer programming language familiar to the skilled artisan); (9) plotting the values and their medians for each of the eight $\Delta C_T$ tables as histograms; and (10) identification of correctly targeted ES cell clone candidates from an inspection of the confidence scores and the $\Delta C_T$ histograms. In a preferred example, the $\Delta C_T$ value for the candidate targeted clone falls within 0.5 to 1.5 cycles greater than the median in 8 out of 8 reference comparisons.

Candidate clones identified by the MOA assay primary screen are confirmed or rejected in a secondary screen, which contains the following steps: (1) use of the genomic DNA from each of the positive candidate ES cell clones, from a larger number of negative clones, and from genomic DNA copy-number standards from mice that carry one or two copies of the LTVEC LacZ-Neo cassette per diploid genome as templates in 8 separate quantitative PCRs on two 384-well plates in which 1 reaction is an upstream PCR (as in the primary screen), one reaction is a downstream PCR (as in the primary screen), 4 reactions are reference PCRs with two reference loci that are different from those used in the primary screen, one reaction is a PCR with primers and a probe that are specific for the LacZ gene of the LTVEC, and one reaction is a PCR with primers and a probe that are specific for the Neo gene of the LTVEC; (2) running the PCRs in a quantitative PCR device, as in the primary screen; (3) calculation, as in the primary screen, of the $\Delta C_T$ values between the upstream PCR and each of the two reference PCRs, between the downstream PCRs and each of the two reference PCRs, between the LacZ PCR and each of the two reference PCRs, and between the Neo PCR and each of the two reference PCRs to create eight $\Delta C_T$ tables; (4) normalization of the $\Delta C_T$ values to positive values; (5) calculation of the median value for each $\Delta C_T$ table; (6) calculation of confidence scores as in the primary screen; and (7) plotting the values and their medians for each of the eight $\Delta C_T$ tables as histograms.

From an inspection of the confidence scores and the $\Delta C_T$ histograms for both the primary and secondary screens, correctly targeted ES clone candidates are either confirmed or rejected. In a preferred example, the $\Delta C_T$ value for the candidate targeted clone falls within 0.5 to 1.5 cycles greater than the median in 12 out of 12 reference comparisons from the combined primary and secondary screens.

To score the number of copies of the LTVEC per diploid genome in the confirmed, correctly targeted ES clones, their $\Delta C_T$ values from the comparisons of the LacZ and Neo PCRs with the two reference PCRs are compared with the $\Delta C_T$ values for the LacZ-Neo copy number standards. Each ES cell clone is scored as having 1, 2 or greater than 2 copies of the LTVEC. For each modified allele project, ES cell clones are screened in groups of 96 (usually fewer than 288 total clones) until 3 clones that score positive in the MOA assay and have a single copy of the LacZ-Neo cassette are identified.

Example 4: Use of FISH to Identify Correctly Targeted LTVECs in ES Cells

Using the LTVEC technology described herein, Applicants knocked out the SM22alpha gene in ES cells. SM22alpha is a 22-kDa smooth muscle cell (SMC) lineage-restricted protein that physically associates with cytoskeletal actin filament bundles in contractile SMCs. The targeted ES cells were then subjected to standard fluorescence in situ hybridization (FISH) on metaphase chromosomal spreads to verify that the gene was appropriately targeted. The experiment was performed with two probes: 1) an SM22alpha gene probe consisting of the unmodified SM22alpha BAC clone used to generate the LTVEC and 2) a LacZ and Neomycin DNA probe which detects only the gene modification made by the targeting event (insertion of LacZ and Neo gene cassettes). Metaphase chromosomal spreads were prepared from cells and hybridization was performed simultaneously with both probes, which were labeled with different colored fluorophores to allow detection of hybridization of each probe within the same spread. A non-targeted ES cell line was analyzed in parallel as a control. As expected, in the control spreads, two alleles of SM22alpha were detected on homologous chromosomal arms, but there was no hybridization of the LacZ-Neo probe. As in controls, in targeted ES cell spreads two alleles were also detected at the same chromosomal location and on homologous chromosomes, but double-labeling with the LacZ-Neo probe was apparent on one of the two chromosomes indicating co-localization of the SM22alpha and LacZ-Neo DNA sequences at that allele of SM22alpha. Importantly, no SM22alpha or LacZ-Neo gene sequences were detected at inappropriate locations in the spreads. Lack of extra integration of SM22alpha gene sequences and co-localization of LacZ-Neo with SM22alpha in one chromosome of a homologous pair strongly suggests that correct targeting of LacZ-Neo to one of the SM22alpha alleles via homologous recombination had occurred.

Example 5: Lowering the Amount of DNA Used to Electroporate ES Cells Improves Targeting Efficiency Standard methods for targeted modification of genes in mouse embryonic stem (ES) cells typically employ 20 to 40 µg of targeting vector in the electroporation procedure. Applicants have discovered that with LTVECs, electroporation with much lower amounts of DNA—in the range of about 1 to 5 µg per $1\times10^7$ cells—doubles the frequency of correctly targeted homologous recombination events while greatly reducing the number of secondary, non-homologous insertion events. This clear improvement in targeting efficiency is important because it significantly reduces the number of ES cells clones that need to be screened to find several positive clones with a correctly targeted, single-copy modification. The associated benefits are reduced cost and increased throughput.

Example 6: Use of the Method of the Invention to Create MA61 Knockout Mice to Study Muscle Atrophy MA61, also called MAFbx, is a recently discovered ubiquitin ligase that is up-regulated in various conditions of muscle atrophy (See U.S. Provisional Application No. 60/264,926, filed Jan. 30, 2001, U.S. Provisional Application No. 60/311,697, filed Aug. 10, 2001, and U.S. Provisional Application (serial number not yet known), filed Oct. 22, 2001, all assigned to Regeneron Pharmaceuticals, Inc., each of which is incorporated herein in its entirety by reference). To further study the biological significance of this gene in muscle atrophy, knockout mice were created using the method of the invention as follows.

First, to obtain a large cloned genomic fragment containing the MA61 gene, a Bacterial Artificial Chromosome (BAC) library was screened with primers derived from the MA61 cDNA sequence. The BAC clone thus obtained was then used to create a Large Targeting Vector for Eukaryotic Cells (LTVEC) as follows. A modification cassette containing a 5' homology box/lacZ gene/polyA/PGK promoter/neo/polyA/3' homology box was engineered. The homology boxes were appended to mark the sites of bacterial homologous recombination during the generation of the LTVEC. The LacZ is a reporter gene that was positioned such that its initiating codon was at the same position as the initiating codon of MA61. Following homologous recombination in bacteria, the modification cassette replaced the MA61 gene. Thus, a MA61 LTVEC was created wherein the MA61 coding sequences in the BAC clone was replaced by the modification cassette engineered as described supra. LTVEC DNA was then prepared, purified, and linearized for introduction into eukaryotic cells as described infra.

A MA61 LTVEC DNA miniprep was prepared (Sambrook, J., E. F. Fritsch And T. Maniatis. Molecular Cloning: A Laboratory Manual, Second Edition, Vols 1, 2, and 3, 1989; Tillett and Neilan, Biotechniques, 24:568-70, 572, 1998; http://www.giagen.com/literature/handbooks/plk-mini/plm_399.pdf) and re-transformed into *E. coli* using electroporation (Sambrook, J., E. F. Fritsch and T. Maniatis, Molecular Cloning: A Laboratory Manual, Second Edition, Vols 1, 2, and 3, 1989) in order to get rid of the plasmid encoding the recombinogenic proteins that are utilized for the bacterial homologous recombination step (Zhang et al., Nat Genet, 20:123-8, 1998; Narayanan et al., Gene Ther, 6:442-7, 1999). Before introducing the MA61 LTVEC into eukaryotic cells, larger amounts of MA61 LTVEC were prepared by standard methodology (http://www.qiagen.com/literature/handbooks/plk/plklow.pdf; Sambrook, J., E. F. Fritsch And T. Maniatis. Molecular Cloning: A Laboratory Manual, Second Edition, Vols 1, 2, and 3, 1989; Tillett and Neilan, Biotechniques, 24:568-70, 572, 1998).

Next, to prepare the MA61 LTVEC for introduction into eukaryotic cells, the MA61 LTVEC was linearized. This was accomplished by digesting with the restriction enzyme NotI, which leaves the modified endogenous gene(s) or chromosomal locus (loci) DNA flanked with long homology arms.

The MA61 LTVEC was then introduced into eukaryotic cells using standard electroporation methodology (Sambrook, J., E. F. Fritsch And T. Maniatis. Molecular Cloning: A Laboratory Manual, Second Edition, Vols 1, 2, and 3, 1989)). The cells in which the MA61 LTVEC was introduced successfully were selected by exposure to a selection agent. Because the selectable marker used in the modification cassette was the neomycin phosphotransferase (neo) gene (Beck, et al., Gene, 19:327-36, 1982), the cells that had taken up the MA61 LTVEC were selected in a medium containing G418; cells that do not have the MA61 LTVEC died whereas cells that have taken up the MA61 LTVEC survived (Santerre, et al., Gene, 30:147-56, 1984).

Eukaryotic cells that have been successfully modified by targeting the MA61 LTVEC into the MA61 locus were identified with the quantitative PCR method TaqMan® (Lie and Petropoulos, Curr Opin Biotechnol, 9:43-8, 1998).

Finally, the genetically modified ES cells were used to create genetically modified, in this case knock out, mice by standard blastocyst injection technology. Thus created were the MA61 knockouts, mice in which the MA61 gene had been deleted.

Both of these knock out mice and wild-type (WT) mice were exposed to atrophy-inducing conditions, created by denervating the mice, and levels of atrophy compared. First, the sciatic nerve was isolated in the mid-thigh region of the right hind limb and transected in the mice. Transection of the sciatic nerve leads to denervation and, over a fourteen-day period, to atrophy in the muscles of the lower limb, specifically the tibialis anterior and gastrocnemius muscles, over a 14-day period. At 7 and 14 days following the denervation, animals were sacrificed by carbon dioxide inhalation. Then the tibialis anterior (TA) and gastrocnemius complex (GA) were removed from the right (denervated) and left (intact) hind limbs, weighed, and frozen at a fixed length in liquid nitrogen cooled isopentane. The amount of atrophy was assessed by comparing the weight of the muscles from the denervated limb with the weight of the muscles from the non-denervated limb.

Muscle atrophy was assessed 7 and 14 days following transection of the right sciatic nerve. The wet weights of the right, denervated muscles were compared to the wet weights of the left, non-denervated muscles. The right:left comparisons are given in Table 2.

| 7 days | Gastrocnemius Complex | | | Tibialis Anterior | | |
|---|---|---|---|---|---|---|
| Genotype | Sample size | Mean | SE | Sample size | Mean | SE |
| WT | 7 | 0.76 | 0.016 | 11 | 0.68 | 0.033 |
| KO | 6 | 0.84 | 0.022 | 11 | 0.80 | 0.015 |

| 14 days | Gastrocnemius Complex | | | Tibialis Anterior | | |
|---|---|---|---|---|---|---|
| Genotype | Sample size | Mean | SE | Sample size | Mean | SE |
| WT | 5 | 0.55 | 0.024 | 5 | 0.62 | 0.023 |
| KO | 5 | 0.80 | 0.019 | 5 | 0.80 | 0.012 |

At 7 and 14 days, the muscles from the knock mice showed significantly (p<0.001) less atrophy than the muscles from the wild type mice. The difference between the knock out and wild type mice was greater at 14 days than at 7 days. While the wild type mice continued to atrophy between 7 and 14 days, the knock out mice showed no additional atrophy.

In summary, the approach of creating LTVECs and directly using them as targeting vectors combined with MOA screening for homologous recombination events in ES cells creates a novel method for engineering genetically modified loci that is rapid, inexpensive and represents a significant improvement over the tedious, time-consuming methods previously in use. It thus opens the possibility of a rapid large scale in vivo functional genomics analysis of essentially any and all genes in an organism's genome in a fraction of the time and cost necessitated by previous methodologies.

Although the foregoing invention has been described in some detail by way of illustration and examples, it will be readily apparent to those of ordinary skill in the art that certain changes and modifications may be made to the teachings of the invention without departing from the spirit or scope of the appended claims.

We claim:

1. A method for detecting the replacement of an endogenous allele with a modified allele by homologous recombination in a mouse embryonic stem (ES) cell, the method comprising: (a) exposing the DNA of the mouse ES cell to a first probe and a second probe, wherein the first probe binds within the endogenous allele but not within the modified allele, and the second probe binds within a reference gene but not within the endogenous allele and not within the modified allele, wherein both probes generate a detectable signal upon binding, and wherein the reference gene is of known copy number; (b) detecting the signal from the binding of the first probe and the signal from the binding of the second probe; and (c) comparing the signal from the binding of the second probe to the signal from the binding of the first probe, and determining from the comparison a copy number of the endogenous allele.

2. The method of claim 1, wherein the modified allele is orthologous to the endogenous allele.

3. The method of claim 2, wherein the modified allele is a human allele orthologous to the endogenous allele.

4. The method of claim 1, wherein the signal from the binding of the first probe is used to determine a first threshold cycle (Ct) value for the endogenous allele and the signal from the binding of the second probe is used to determine a second Ct value for the reference gene, and wherein copy number of the endogenous mouse allele is determined by comparing the first Ct value and the second Ct value.

5. The method of claim 1, wherein the copy number of the endogenous allele is one.

6. The method of claim 1, wherein the copy number of the endogenous allele is zero.

7. The method of claim 1, wherein the Ct value of the second probe is the same in targeted ES cells as compared to the Ct value in non-targeted cells.

8. The method of claim 1, wherein the modified allele comprises a regulatory element.

9. The method of claim 1, wherein the modified allele comprises a protein-coding sequence.

10. The method of claim 9, wherein the protein-coding sequence contains an alteration as compared to a protein-coding sequence within the endogenous allele.

11. The method of claim 10, wherein the alteration is selected from the group consisting of a deletion, an insertion and a substitution.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Mouse OCR10 gene primer

<400> SEQUENCE: 1
agctaccagc tgcagatgcg ggcag                                    25

<210> SEQ ID NO 2
<211> LENGTH: 28
<212> TYPE: DNA
<213> ORGANISM: Artificial Sequence
<220> FEATURE:
<223> OTHER INFORMATION: Mouse OCR10 gene primer

```
<400> SEQUENCE: 2
ctccccagcc tgggtctgaa agatgacg                                      28

<210> SEQ ID NO 3
<211> LENGTH: 24
<212> TYPE: DNA
<213> ORGANISM: Artificial Sequence
<220> FEATURE:
<223> OTHER INFORMATION: Mouse OCR10 gene primer

<400> SEQUENCE: 3
gacctcactt gctacactga ctac                                          24

<210> SEQ ID NO 4
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 4
acttgtgtag gctgcagaag gtctcttg                                      28

<210> SEQ ID NO 5
<211> LENGTH: 1799
<212> TYPE: DNA
<213> ORGANISM: Artificial Sequence
<220> FEATURE:
<223> OTHER INFORMATION: Mouse OCR10 cDNA

<400> SEQUENCE: 5
ccccgggctt cctgttctaa taagaatacc tcctaggtcc cccatgggct aacctcatct     60
ttggtactca acagggtct tctttatgag cttcggacca gctctttga tgtggcaggg     120 actgaccctg ggtggggaag ccactcagtg catgacccca gctggttcac cacatatacc    180
acatactttt cttgcaggtc tgggacacag catgccccgg ggcccagtgg ctgccttact    240
cctgctgatt ctccatggag cttggagctg cctggaccct acttgctaca ctgactacct    300
ctggaccatc acctgtgtcc tggagacacg gagccccaac cccagcatac tcagtctcac    360
ctggcaagat gaatatgagg aacttcagga ccaagagacc ttctgcagcc tacacaagtc    420
tggccacaac accacacata tatggtacac gtgccatatg cgcttgtctc aattcctgtc    480
cgatgaagtt ttcattgtca acgtgacgga ccagtctggc aacaactccc aagagtgtgg    540
cagctttgtc ctggctgaga gcatcaagcc agctcccccc ttgaacgtga ctgtggcctt    600
ctcaggacgc tatgatatct cctgggactc agcttatgac gaaccctcca actacgtgct    660
gagaggcaag ctacaatatg agctgcagta tcggaacctc agagacccct atgctgtgag    720
gccggtgacc aagctgatct cagtggactc aagaaacgtc tctcctccct gaagagttcc    780
acaaagattc tagctaccag ctgcagatgc gggcagcgcc tcagccaggc acttcattca    840
gggggacctg gagtgagtgg agtgaccccg tcatctttca gacccaggct ggggagcccg    900
aggcaggctg gaccctcac atgctgctgc tcctggctgt cttgatcatt gtcctggttt    960
tcatgggtct gaagatccac ctgccttgga ggctatggaa aaagatatgg gcaccagtgc   1020 ccaccctga gagtttcttc cagcccctgt acagggagca cagcgggaac ttcaagaaat   1080
gggttaatac ccctttcacg gcctccagca tagagttggt gccacagagt tccacaacaa   1140
```

```
catcagcctt acatctgtca ttgtatccag ccaaggagaa gaagttcccg gggctgccgg    1200
gtctggaaga gcaactggag tgtgatggaa tgtctgagcc tggtcactgg tgcataatcc    1260
ccttggcagc tggccaagcg gtctcagcct acagtgagga gagagaccgg ccatatggtc    1320
tggtgtccat tgcacacagtg actgtgggag atgcagaggg cctgtgtgtc tggccctgta    1380
gctgtgagga tgatggctat ccagccatga acctggatgc tggcagagag tctggtccta    1440
attcagagga tctgctcttg gtcacagacc ctgcttttct gtcttgtggc tgtgtctcag    1500
gtagtggtct caggcttggg ggctccccag gcagcctact ggacaggttg aggctgtcat    1560
ttgcaaagga aggggactgg acagcagacc caacctggag aactgggtcc ccaggagggg    1620
gctctgagag tgaagcaggt tccccccctg gtctggacat ggacacattt gacagtggct    1680
ttgcaggttc agactgtggc agcccgtgg agactgatga aggacccct cgaagctatc    1740 tccgccagtg ggtggtcagg acccctccac ctgtggacag tggagcccag agcagctag    1799

<210> SEQ ID NO 6
<211> LENGTH: 529
<212> TYPE: PRT
<213> ORGANISM: Artificial Sequence
<220> FEATURE:
<223> OTHER INFORMATION: Mouse OCR10 protein

<400> SEQUENCE: 6

Met Pro Arg Gly Pro Val Ala Ala Leu Leu Leu Ile Leu His Gly
 1               5                  10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Lys Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Met Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
```

|  |  |  |  | 245 |  |  |  |  | 250 |  |  |  |  | 255 |  |
|---|---|---|---|---|---|---|---|---|---|---|---|---|---|---|---|

His Leu Pro Trp Arg Leu Trp Lys Lys Ile Trp Ala Pro Val Pro Thr
        260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
        290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
                340                 345                 350

Ala Ala Gly Gln Ala Val Ser Ala Tyr Ser Glu Glu Arg Asp Arg Pro
                355                 360                 365

Tyr Gly Leu Val Ser Ile Asp Thr Val Thr Val Gly Asp Ala Glu Gly
        370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415

Leu Val Thr Asp Pro Ala Phe Leu Ser Cys Gly Cys Val Ser Gly Ser
                420                 425                 430

Gly Leu Arg Leu Gly Gly Ser Pro Gly Ser Leu Leu Asp Arg Leu Arg
                435                 440                 445

Leu Ser Phe Ala Lys Glu Gly Asp Trp Thr Ala Asp Pro Thr Trp Arg
        450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
                500                 505                 510

Gln Trp Val Val Arg Thr Pro Pro Val Asp Ser Gly Ala Gln Ser
        515                 520                 525

Ser